(12) United States Patent
Miura et al.

(10) Patent No.: US 7,678,940 B2
(45) Date of Patent: Mar. 16, 2010

(54) PROCESS FOR PRODUCING CARBOXYLIC ACID

(75) Inventors: Hiroyuki Miura, Himji (JP); Hidetaka Kojima, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 126 days.

(21) Appl. No.: 11/922,339

(22) PCT Filed: Jul. 11, 2006

(86) PCT No.: PCT/JP2006/314124

§ 371 (c)(1),
(2), (4) Date: Dec. 17, 2007

(87) PCT Pub. No.: WO2007/007891

PCT Pub. Date: Jan. 18, 2007

(65) Prior Publication Data

US 2009/0036710 A1    Feb. 5, 2009

(30) Foreign Application Priority Data

Jul. 14, 2005 (JP) .............................. 2005-205740

(51) Int. Cl.
*C07C 51/42* (2006.01)
(52) U.S. Cl. .................................. 562/608
(58) Field of Classification Search .................. None
See application file for complete search history.

(56) References Cited

U.S. PATENT DOCUMENTS 4,039,395 A * 8/1977 Eby .......................... 203/38

FOREIGN PATENT DOCUMENTS

| GB | 1 350 726 B | 4/1974 |
|---|---|---|
| JP | 52-023016 A | 2/1977 |
| JP | 57-55695 A | 11/1982 |
| JP | 6-40999 A | 2/1994 |
| WO | WO-02/062740 A1 | 8/2002 |

\* cited by examiner

*Primary Examiner*—Karl J Puttlitz
(74) *Attorney, Agent, or Firm*—Birch, Stewart, Kolasch & Birch, LLP.

(57) ABSTRACT

A process for producing a purified carboxylic acid having "n+1" carbon atoms comprises feeding a carboxylic acid stream containing a carboxylic acid having "n+1" carbon atoms, a hydrogen halide, a lower boiling point (bp) component, a higher bp component, and others to a first distillation column; separating a lower bp fraction containing part of the lower bp component and a higher bp fraction containing part of the higher bp component in the first column; withdrawing a side stream containing at least the carboxylic acid by side cut from the first column; feeding the side stream to a second distillation column; separating a lower bp fraction containing part of the lower bp component and a higher bp fraction containing part of the higher bp component in the second column; and withdrawing a side stream containing the carboxylic acid by side cut from the second column to recover a purified carboxylic acid; and the process further comprises feeding at least one first component (A) selected from the group consisting of an alcohol, corresponding to the carboxylic acid, having "n" carbon atom(s), and an ester of the alcohol with the carboxylic acid to the first column, and if necessary water. Such a process ensures reduction of the concentration of the hydrogen halide in the purified carboxylic acid.

14 Claims, 2 Drawing Sheets

PROCESS FOR PRODUCING CARBOXYLIC ACID

TECHNICAL FIELD

The present invention relates to a process useful for reducing a concentration of a hydrogen halide contained in a carboxylic acid as a final product by inhibiting condensation of the hydrogen halide (e.g., hydrogen iodide) in a distillation column, for example, a distillation process, and a production process of a carboxylic acid (e.g., acetic acid); and a system for producing a carboxylic acid.

BACKGROUND ART

In a production of acetic acid, when a solution containing water, hydrogen iodide, iodide ion (hereinafter, hydrogen iodide and/or iodide ion are/is sometimes simply referred to as hydrogen iodide), methyl iodide, methyl acetate, acetic acid, and others is distilled and purified, hydrogen iodide is condensed in a distillation column thereof due to interaction between hydrogen iodide and water. Accordingly, even when such a mixture is distilled, hydrogen iodide cannot be efficiently removed, and as a result, it is difficult to sufficiently reduce a concentration of hydrogen iodide in acetic acid as a final product. Moreover, high concentration of hydrogen iodide accelerates corrosion of the distillation column and peripheral equipment.

In order to reduce the concentration of the hydrogen iodide in the distillation column, it is proposed that a component such as methanol is supplied from a middle part or plate of the distillation column to convert hydrogen iodide to methyl iodide. Japanese Patent Application Laid-Open No. 40999/1994 (JP-6-40999A, Patent Document 1) discloses a process for the production of acetic acid which the process comprises:

feeding methanol and carbon monoxide to a carbonylation zone in which there is held a liquid reaction composition comprising: a rhodium catalyst; methyl iodide; an iodide salt; water at a concentration of up to about 10% by weight; methyl acetate at a concentration of at least 2% by weight; and acetic acid, introducing the liquid reaction composition to a flash zone, recycling the liquid fraction from the flash zone to the reaction zone, and recovering acetic acid product from the flash zone vapor fraction by use of a single distillation zone by:

introducing the vapor fraction from the flash zone into the distillation zone, removing from the head of the distillation zone a light ends recycle stream, and removing from the distillation zone an acid product stream having a water concentration of less than 1500 ppm and a propionic acid concentration of less than 500 ppm. This document also describes that the acetic acid product is passed through an ion exchange resin (anion exchange resin) bed to remove iodide contaminants. Incidentally, in Patent Document 1, the product acid stream is withdrawn from the bottom of the distillation zone or the second plate from the bottom of the distillation zone.

Further, this document mentions that the build up of hydrogen iodide component is prevented by introducing a small feed of methanol to the distillation zone, preferably below the feed point of the zone, to convert the hydrogen iodide to methyl iodide which is removed in the light ends recycle stream; up to 5000 ppm hydrogen iodide in the feed can be treated in this way; and by operating the distillation zone at a sufficiently elevated pressure, for the relatively high concentration of methyl acetate in the distillation zone, the hydrogen iodide is converted to methyl iodide which is removed in the light ends recycle stream.

However, even in these processes, hydrogen iodide cannot be effectively eliminated. Moreover, it is not preferred to increase pressure or temperature for converting hydrogen iodide to methyl iodide, because corrosion due to hydrogen iodide is accelerated. Incidentally, even when acetic acid having a water concentration of not more than 1500 ppm is removed, it is impossible to reduce the concentration of hydrogen iodide in the acetic acid to not more than 12 ppm due to affinity between hydrogen iodide and water (e.g., formation of the highest azeotrope). In addition, in order to further reduce the concentration of hydrogen iodide, it is necessary to use an anion exchange resin. As a result, the costs for the treatment increase. Moreover, since the product acid stream is removed at the base of the distillation zone, it is impossible to efficiently separate and recover the entrained rhodium catalyst. In addition, the operating trouble occurs due to blockage, or the quality of product is deteriorated, as well as it is unfavorable in costs. Therefore, it is difficult to conduct these processes industrially. Moreover, in order to avoid the above problems, equipment for separating or recovering the rhodium catalyst is required separately.

Japanese Patent Application Laid-Open No. 23016/1977 (JP-52-23016A, Patent Document 2) discloses a process for the removal and recovery of iodine-containing components and the drying of acetic acid, which comprises introducing a stream of acetic acid containing water, methyl iodide and hydrogen iodide into an intermediate point of a first distillation zone, removing, as an overhead fraction, from the first distillation zone most of the methyl iodide and portion of water, removing most of the hydrogen iodide from the bottom of the first distillation zone, withdrawing a stream from a middle section of the first distillation zone and introducing the stream into the upper section of a second distillation zone, introducing a stream of methanol into the lower section of the second distillation zone, removing from overhead of the second distillation zone a stream containing the remainder of water and methyl iodide present together with any methyl acetate, and withdrawing at or near the bottom of the second distillation zone a stream of a product acetic acid essentially dry and substantially free of hydrogen iodide and methyl iodide.

This document discloses that, in the process distilling the side cut fraction provided from the first distillation column in the second distillation column to recover acetic acid, the process does not require recycling of a side cut fraction, containing hydrogen iodide, from the second distillation column to the first distillation column since methanol is introduced into the second distillation column and hydrogen iodide is chemically removed.

Such a process does not require condensation of hydrogen iodide in the distillation column and removal of hydrogen iodide by side cut. However, the concentration of hydrogen iodide contained in product acetic acid cannot be sufficiently reduced.

Great Britain Patent No. 1350726 specification (Patent Document 3) discloses a purification process of a monocarboxylic acid component containing water and alkyl halide and/or hydrogen halide contaminants, which the process comprises introducing the monocarboxylic acid component containing water and alkyl halide and/or hydrogen halide contaminants into the upper half of a distillation zone, removing an overhead fraction containing most of water and the alkyl halide, withdrawing a stream from the middle part of the zone and below the point of the introduction of the zone to eliminate most of hydrogen halide present in the zone, and withdrawing a product monocarboxylic acid stream from the bottom part of the zone to obtain a product monocarboxylic acid stream being essentially dry and substantially free from any alkyl halide and hydrogen halide. The document describes that the liquid composition of carboxylic acid having a water content of about 3 to 8% by weight forms a peak of a hydrogen halide concentration at the intermediate part of the distillation column, and if a side stream is withdrawn from the intermediate part of the distillation column, a monocarboxylic acid in which almost all of hydrogen halide is removed can be obtained. Further, the document also discloses that in the case of subjecting a reaction product obtained from a reaction of methanol with carbon monoxide to a flash distillation, followed by introducing a fraction separated by the flash distillation into the distillation column, hydrogen iodide is condensed in a side stream from the intermediate part of the distillation column and removed.

However, in such a process, because of fluctuation of the peak position of hydrogen halide concentration due to variable factors (such as temperature, and pressure) in the distillation step, contamination of an acetic acid as a final product with hydrogen iodide sometimes occurs. Further, due to affinity between hydrogen iodide and water, it is impossible to remarkably reduce the hydrogen iodide concentration in the acetic acid.

Incidentally, WO02/062740 publication (Patent Document 4) discloses a continuous process for producing acetic acid comprising the following steps (a) to (d): (a) a step for reacting methanol with carbon monoxide; (b) a step for withdrawing a stream of a reaction medium from a reactor and vaporizing a portion of the withdrawn medium in a flashing step; (c) a step for distilling the flashed vapor utilizing two distillation columns to form a liquid acetic acid product stream; and (d) a step for removing iodides from the liquid acetic acid product stream such that the product stream has an iodide content of less than 10 ppb iodide by (i) contacting the liquid acetic acid product stream with an anionic ion exchange resin at a temperature of not lower than about 100° C. followed by contacting the resultant stream with a silver or mercury exchanged ion exchange substrate or (ii) contacting the liquid acetic acid product stream with a silver or a mercury exchanged ion exchange substrate at a temperature of not lower than about 50° C. As described above, according to the Patent Document 4, the iodides are removed from the acetic acid product stream with the use of the anionic ion exchange resin and/or a guard bed. However, in such a process, since it is impossible to remove carbonyl impurities having higher boiling points (such as an aldehyde, a carboxylic acid and an ester), a result in a potassium permanganate test which is a standard of a product acetic acid is deteriorated and the quality of the product is lowered. Further, it is difficult to remove higher boiling point components such as metal impurities and sulfate. Therefore, in order to obtain acetic acid satisfying a standard of a product acetic acid, it is necessary to install an incidental equipment for treating an acetic acid stream.

Incidentally, to remove iodides by a silver or mercury exchanged ion exchange resin is based on a monomolecular nucleophilic substitution (SN1) reaction, called as acetolysis, which is well-known in the field of organic chemistry. That is, a substrate iodide (RX) is decomposed into a carbonium ion ($R^+$) and an anion ($X^-$) by solvation of acetic acid (heterolysis), and the generated $R^+$ quickly reacts with acetic acid as a nucleophilic reagent. This SN1 reaction is promoted by Ag, Hg or Cu which can form a coordinate bond together with an unshared electron pair of the leaving group (X).

In the above-mentioned SN1 reaction, the dissociation energy of the bond R—X becomes smaller as the carbon number of the R (or the carbon chain) increases (that is, in the order of $CH_3$, $C_2H_5$, $C_3H_7$, $C_4H_9$ . . . ). For example, the dissociation energy of $CH_3I$ and that of $C_2H_5I$ are 234 kJ/mol and 224 kJ/mol, respectively. Thus, higher iodide gets easily removable by a guard bed.

However, in the case where the R is hydrogen atom, it is known that the dissociation energy of the bond R—X is extremely large. For example, the dissociation energy of hydrogen iodide (HI) is 299 kJ/mol, and it is extremely difficult to separate and remove hydrogen iodide by a guard bed in principle. Moreover, thus obtained acetic acid is industrially and/or commercially insufficient in the light of the quality of the product and the corrosion of the equipment.

Japanese Patent No. 55695/1982 (JP-57-55695B, Patent Document 5) discloses a process for removing iodine from acetic acid, which comprises introducing an acetic acid stream containing iodine as an impurity into a first distillation column intermediate from the both ends thereof, introducing into the first distillation column intermediate from the both ends thereof a hydroxide of an alkali metal, and an acetate of an alkali metal, and/or hypophosphorous acid, withdrawing a product stream overhead from the first distillation column, introducing the product stream into a second distillation column intermediate from the both ends thereof, withdrawing an acetic acid stream substantially free from iodine from the lower part of the second distillation column, and withdrawing an overhead fraction containing iodine from the second distillation column. However, removal of hydrogen iodide by introducing the above reagent such as an alkali metal hydroxide into the first distillation column having a very high concentration of hydrogen iodide requires an extremely amount of the reagent. In addition, the amount of an alkali metal iodide generated by the treatment increases. Therefore, it is environmentally and economically disadvantageous in the light of separation or disposition. Moreover, since a large amount of potassium acetate generated from neutralization between acetic acid and the alkali metal hydroxide comes to be mixed in the product, the yield of acetic acid is deteriorated. Further, in the above-mentioned process, acetic acid is withdrawn as an overhead from the first distillation column. However, in the overhead, the proportions of hydrogen iodide and water are large. In such an environment, methyl iodide is hydrolyzed to generate hydrogen iodide, and the generated hydrogen iodide is allowed to be mixed in a feeding stream to the second distillation column.

[Patent Document 1] JP-6-40999A (Claims, and Paragraph Number [0043])

[Patent Document 2] JP-52-23016A (Claims, page 5, the lower right column, page 7, the lower left column to the lower right column, and Example 1)

[Patent Document 3] Great Britain Patent No. 1350726 specification (Claims, page 2, lines 66 to 76, and Example 1)

[Patent Document 4] WO02/062740 publication (Claim 1)

[Patent Document 5] JP-57-55695B (Claim 1)

DISCLOSURE OF THE INVENTION

Problems to be Solved by the Invention

It is therefore an object of the present invention to provide a process for producing a carboxylic acid, in which a concentration of a hydrogen halide contained in a carboxylic acid as a final product can be reduced by inhibiting condensation of a hydrogen halide in a distillation column and corrosion of the distillation column can be decreased; and a producing system thereof.

It is another object of the present invention to provide a process for producing a purified carboxylic acid by reducing concentration of such a halide as not only a hydrogen halide but also a halogenated hydrocarbon; and a producing system thereof.

It is still another object of the present invention to provide a process for producing a highly pure carboxylic acid by efficiently removing lower boiling point impurities (lower bp impurities) and higher boiling point impurities (higher bp impurities); and a producing system thereof.

It is a further object of the present invention to provide a process for producing an objective carboxylic acid obtained by efficient purification of a reaction mixture which is obtained from a carbonylation reaction of an alcohol or a derivative thereof; and a producing system thereof.

Means to Solve the Problems

The inventors of the present invention made intensive studies to achieve the above objects and finally found that, in a process for producing a purified carboxylic acid, which comprises purifying a carboxylic acid stream containing a carboxylic acid having "n+1" carbon atoms and impurities such as a hydrogen halide with the use of first and second distillation columns; by feeding water and/or at least one component (A) (a first component) selected from the group consisting of an alcohol having "n" carbon atom(s) corresponding to the carboxylic acid and an ester of the alcohol with the carboxylic acid to at least the first distillation column, the hydrogen halide can be effectively separated by conversion of the hydrogen halide to a lower boiling point component. The present invention was accomplished based on the above findings.

That is, the present invention includes a process for producing a carboxylic acid (or a purified carboxylic acid) having "n+1" carbon atoms, which comprises feeding a carboxylic acid stream containing at least a carboxylic acid having "n+1" carbon atoms, a hydrogen halide, a lower boiling point component (hereinafter, sometimes referred to as a lower bp component) and a higher boiling point component (hereinafter, sometimes referred to as a higher bp component) to a first distillation column, separating a lower boiling point fraction (a first lower boiling point fraction) containing part of the lower boiling point component and a higher boiling point fraction (a first higher boiling point fraction) containing part of the higher boiling point component in the first distillation column, withdrawing a side stream (a first side stream) containing at least the carboxylic acid having "n+1" carbon atoms by side cut from the first distillation column, feeding the side stream (the first side stream) to a second distillation column, separating a lower boiling point fraction (a second lower boiling point fraction) containing part of the lower boiling point component and a higher boiling point fraction (a second higher boiling point fraction) containing part of the higher boiling point component in the second distillation column, and withdrawing a side stream (a second side stream) containing the carboxylic acid having "n+1" carbon atoms by side cut from the second distillation column to recover a carboxylic acid (or a purified carboxylic acid) having "n+1" carbon atoms;

which further comprises feeding water and/or at least one component (A) (a first component) selected from the group consisting of an alcohol, corresponding to the carboxylic acid, having "n" carbon atom(s), and an ester of the alcohol with the carboxylic acid to at least the first distillation column.

The hydrogen halide may be usually separated as a lower boiling point component by feeding water, the first component (A), or both water and the first component (A). By such a process, the hydrogen halide in the distillation column can be efficiently removed, and the concentration of the hydrogen halide contained in a product carboxylic acid can be extremely reduced. Moreover, condensation of the hydrogen halide in the distillation column can be inhibited, and corrosion of the distillation column can be also decreased.

In the production process, in the case of feeding the first component (A) alone, the first component (A) is fed to the first distillation column from a lower position relative to a side stream port (first side stream port) for conducting side cut of the side stream (the first side stream) containing the carboxylic acid having "n+1" carbon atoms. Moreover, water, or water and the component (A) may be fed to the first distillation column from an upper position relative to the side stream port (the first side stream port) for conducting side cut of the side stream (the first side stream) containing the carboxylic acid having "n+1" carbon atoms. In the first distillation column, at least water (e.g., water and the component (A)) may be fed from an upper position relative to the side stream port (the first side stream port) for conducting side cut of the side stream (the first side stream) containing the carboxylic acid having "n+1" carbon atoms, and the first component (A) (e.g., the alcohol) may be fed from a lower position relative to the side stream port (the first side stream port). By such a process, the amount of the hydrogen halide contained in the carboxylic acid stream obtained by side cut from the first distillation column can be effectively reduced.

Each of the feed proportion of the first component (A) and that of water may satisfy the following (i), (ii), or both of (i) and (ii). By such a process, the hydrogen halide in the acetic acid stream obtained by side cut can be more effectively removed.

(i) The feed proportion is 1 to 10,000 mol relative to 1 mol of the hydrogen halide contained in the carboxylic acid stream fed to the first distillation column.

(ii) The feed proportion is 0.02 to 50% by mol relative to the total amount of the carboxylic acid having "n+1" carbon atoms contained in the carboxylic acid stream fed to the first distillation column.

The production process may comprise further feeding to the second distillation column at least one component (B) (a second component) selected from the group consisting of (b-1) an alcohol, corresponding to the carboxylic acid having "n+1" carbon atom, having "n" carbon atom(s), (b-2) an ester of the alcohol with the carboxylic acid having "n+1" carbon atoms, (b-3) an alkali metal hydroxide, (b-4) an alkali metal acetate and (b-5) a hypophosphorous acid. Moreover, the second component (B) may be fed to the second distillation column from at least one of upper and lower positions relative to a side stream port (a second side stream port) for conducting side cut of the side stream (the second side stream) containing the carboxylic acid having "n+1" carbon atoms. Regarding the second component (B), the total of the feed proportion of the component (b-1) and the feed proportion of the component (b-2) may satisfy the following (i), (ii), or both of (i) and (ii). Moreover, the feed proportion of the component (b-3) may satisfy the following (iii), (iv), or both of (iii) and (iv).

(i) The total of the feed proportion of the component (b-1) and the feed proportion of the component (b-2) is 1 to 10,000 mol relative to 1 mol of the hydrogen halide contained in the carboxylic acid stream fed to the second distillation column.

(ii) The total of the feed proportion of the component (b-1) and the feed proportion of the component (b-2) is 0.02 to 50% by mol relative to the total amount of the carboxylic acid having "n+1" carbon atoms contained in the carboxylic acid stream fed to the second distillation column.

(iii) The feed proportion of the component (b-3) is 1 to 20,000 mol relative to 1 mol of the hydrogen halide contained in the carboxylic acid stream fed to the second distillation column.

(iv) The amount of the carboxylic acid having "n+1" carbon atoms contained in the carboxylic acid stream fed to the second distillation column is 30 to 300,000 mol relative to 1 mol of the component (b-3).

In such a process, the amount of the hydrogen halide contained in the acetic acid stream obtained by side cut from the second distillation column can be more extremely reduced.

The production process may comprise continuously allowing an alcohol having "n" carbon atom(s) or a derivative thereof to react with carbon monoxide at a hydrogen partial pressure of 1 to 150 kPa in a vapor phase of the reaction system in the presence of a catalytic system comprising a metal catalyst component and an alkyl halide, and water in a proportion of 0.1 to 10% by weight relative to a whole liquid-phase reaction system, continuously withdrawing the reaction mixture from the reaction system, feeding the reaction mixture to a catalyst-separating column, separating a higher boiling point fraction (a third higher boiling point fraction) containing the metal catalytic component, and a lower boiling point fraction (a third lower boiling point fraction), and feeding the lower boiling point fraction (the third lower boiling point fraction) as a carboxylic acid stream to the first distillation column.

The side stream (the second side stream) obtained by side cut from the second distillation column may be further contacted with an ion exchange resin having a halide-removability (ability for removing a halide) or a halide-adsorbability (ability for adsorbing a halide) to produce a purified carboxylic acid having "n+1" carbon atoms. By such a process, the halide (e.g., a halogenated hydrocarbon) in the product carboxylic acid can be efficiently removed.

The lower boiling point fraction withdrawn from the first distillation column and/or the second distillation column may be fed to the reaction system. Moreover, the lower boiling point fraction withdrawn from the first distillation column and/or the second distillation column may contain an alkyl halide, an alkyl ester of a carboxylic acid having "n+1" carbon atoms, an aldehyde having "n+1" carbon atoms, and water; and the process may further comprise subjecting the lower boiling point fraction to an aldehyde separation step;

separating, in the aldehyde separation step, a lower boiling point fraction (a fourth lower boiling point fraction) containing the aldehyde, and a higher boiling point fraction (a fourth higher boiling point fraction) containing the alkyl halide, the alkyl ester of the carboxylic acid, and water; and recycling the higher boiling point fraction (the fourth higher boiling point fraction) to the reaction system.

By such a process, cycling of an aldehyde to the reaction system or the distillation column can be inhibited, and the alkyl halide, the alkyl eater of the carboxylic acid, water, and others can be reusable to the reaction. Therefore, it is advantageous in costs. Further, the lower boiling point fraction (the first lower boiling point fraction) from the first distillation column may be fed to the first distillation column. In such a process, separability between the carboxylic acid (e.g., acetic acid) and water can be enhanced by adding a component (e.g., the alkyl halide, and the alkyl ester of a carboxylic acid) azeotropic with water to the distillation column.

The production process may comprise continuously allowing methanol react with carbon monoxide at a hydrogen partial pressure of 5 to 100 kPa in a vapor phase of the reaction system in the presence of a catalytic system comprising a metal catalyst of the group 8 metal of the Periodic Table, an alkali metal iodide and an alkyl iodide, and water in a proportion of 0.1 to 5% by weight relative to a whole liquid-phase reaction system, continuously withdrawing the reaction mixture from the reaction system, feeding the reaction mixture to a catalyst-separating column, separating a higher boiling point fraction (a third higher boiling point fraction) containing the metal catalyst and the alkali metal iodide, and a lower boiling point fraction (a third lower boiling point fraction) containing acetic acid, an alkyl iodide, methyl acetate, water and propionic acid, feeding the lower boiling point fraction (the third lower boiling point fraction) as a carboxylic acid stream to the first distillation column, separating a lower boiling point fraction (a first lower boiling point fraction) containing part of the alkyl iodide, the methyl acetate and water, and a higher boiling point fraction (a first higher boiling point fraction) containing part of water and propionic acid in the first distillation column, withdrawing a side stream (a first side stream) containing at least the acetic acid by side cut from the first distillation column, feeding the side stream (the first side stream) to the second distillation column, separating a lower boiling point fraction (a second lower boiling point fraction) containing part of the alkyl iodide, the methyl acetate and water, and a higher boiling point fraction (a second higher boiling point fraction) containing part of water and propionic acid in the second distillation column, withdrawing a side stream (a second side stream) containing the acetic acid (the purified acetic acid) by side cut from the second distillation column to recover acetic acid.

In the production process, water and/or at least one first component (A) selected from the group consisting of methanol and methyl acetate may be fed to at least the first distillation column. Such a production process may comprise further feeding to the second distillation column at least one component (B) (second component) selected from the group consisting of (b-1) methanol, (b-2) methyl acetate, (b-3) potassium hydroxide, (b-4) potassium acetate and (b-5) hypophosphorous acid. By such a process, even in an acetic acid stream produced by the carbonylation reaction of methanol, efficient purification by the distillation column is ensured, and a purified acetic acid in which the amount of the hydrogen iodide is drastically reduced can be produced.

The present invention also includes a system for producing a carboxylic acid, which comprises a first distillation column for separating, from a carboxylic acid stream containing at least a carboxylic acid having "n+1" carbon atoms, a hydrogen halide, a lower boiling point component and a higher boiling point component, a lower boiling point fraction (a first lower boiling point fraction) containing part of the lower boiling point component and a higher boiling point fraction (a first higher boiling point fraction) containing part of the higher boiling point component, and withdrawing a side stream (a first side stream) containing at least the carboxylic acid having "n+1" carbon atoms by side cut, and a second distillation column for separating a lower boiling point fraction (a second lower boiling point fraction) containing part of the lower boiling point component and a higher boiling point fraction (a second higher boiling point fraction) containing part of the higher boiling point component from the side stream (the first side stream) from the first distillation column, and withdrawing a side stream (a second side stream) containing a carboxylic acid (a purified carboxylic acid) having "n+1" carbon atoms by side cut to recover the side stream (the second side stream), wherein water, and/or water and a component (A) (first component) selected from the group consisting of an alcohol, corresponding to the carboxylic acid, having "n" carbon atom(s), and an ester of the alcohol with the carboxylic acid is fed to at least the first distillation column.

Moreover, the production system may comprise a reaction system for continuously allowing an alcohol having "n" carbon atom(s) or a derivative thereof to react with carbon monoxide at a hydrogen partial pressure of 1 to 150 kPa in a vapor phase of the reaction system in the presence of a catalytic system comprising a metal catalytic component and an alkyl halide, and water in a proportion of 0.1 to 10% by weight relative to a whole liquid-phase reaction system, a catalyst-separating column for separating a higher boiling point fraction (a third higher boiling point fraction) containing the metal catalytic component and a lower boiling point fraction (a third lower boiling point fraction) as a carboxylic acid stream from a reaction mixture continuously withdrawn from the reaction system, a first distillation column for separating a lower boiling point fraction (a first lower boiling point fraction) containing part of the lower boiling point component and a higher boiling point fraction (a first higher boiling point fraction) containing part of the higher boiling point component from the carboxylic acid stream from the catalyst-separating column, and withdrawing the side stream (the first side stream) containing at least the carboxylic acid having "n+1" carbon atoms by side cut, a second distillation column for separating a lower boiling point fraction (a second lower boiling point fraction) containing part of the lower boiling point component and a higher boiling point fraction (a second higher boiling point fraction) containing part of the higher boiling point component from the side stream (the first side stream) from the first distillation column, and withdrawing a side stream (a second side stream) containing a carboxylic acid (a purified carboxylic acid) having "n+1" carbon atoms by side cut to recover the side stream (the second side stream), and a halide-removing column for removing a halide from the side stream (the second side stream) containing the carboxylic acid (the purified carboxylic acid) from the second distillation column, and obtaining a carboxylic acid (a purified carboxylic acid) having "n+1" carbon atoms.

In the production system, the halide-removing column may be equipped with an ion exchange resin therein, and the ion exchange resin has a halide-removability or a halide-adsorbability for removing the halide by contacting with the side stream (the second side stream) from the second distillation column.

Effect of the Invention

According to the present invention, in a process for producing a purified carboxylic acid, which comprises purifying a carboxylic acid stream containing a carboxylic acid having "n+1" carbon atoms, and impurities such as a hydrogen halide by means of first and second distillation columns, since (i) water, and/or (ii) at least one component (A) selected from the group consisting of an alcohol having "n" carbon atom(s) corresponding to the carboxylic acid, and an ester of the alcohol with the carboxylic acid are/is fed to at least the first distillation column (particularly, in the case of feeding the component (A) alone, the component (A) is fed from a lower position relative to a side stream port for conducting side cut of the carboxylic acid); the hydrogen halide can be converted to a lower boiling point component and efficiently separated as a lower boiling point fraction. As a result, the concentration of the hydrogen halide contained in a carboxylic acid as a final product can be reduced. Moreover, the condensation of the hydrogen halide in the distillation column can be inhibited, and therefore corrosion of the distillation column can be decreased. Further, by further contacting a fraction containing a purified carboxylic acid withdrawn from the second distillation column with an ion exchange resin having halide-removability or halide-adsorbability, the concentration of such the halide as not only the hydrogen halide but also a halogenated hydrocarbon can be also reduced. Moreover, according to the present invention, lower bp impurities and higher bp impurities can be efficiently removed, and a highly pure carboxylic acid can be produced. Furthermore, an efficiently purified objective carboxylic acid can be produced even from a reaction mixture obtained by a carbonylation reaction of an alcohol and/or a derivative thereof.

DETAILED DESCRIPTION OF THE INVENTION

Figure 1:
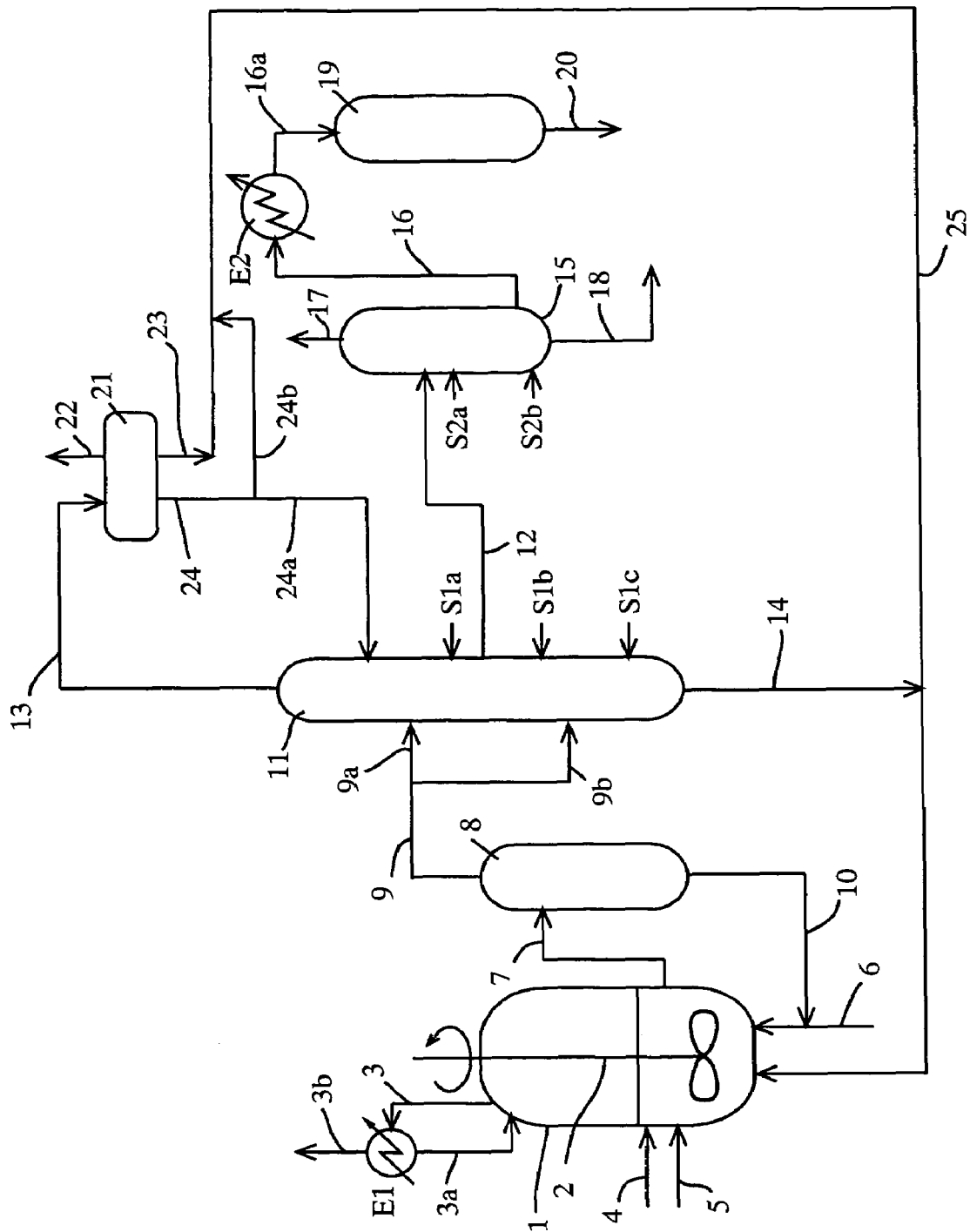
FIG. 1 is a flow diagram for illustrating an embodiment of a production process of a carboxylic acid of the present invention.

The present invention shall now be described in detail with reference if necessary to the attached drawings. FIG. 1 is a flow diagram for explaining a production process of a carboxylic acid of the present invention.

The embodiment of FIG. 1 shows a process for producing a purified acetic acid from a reaction mixture generated by a continuous carbonylation reaction of methanol with carbon monoxide in the presence of a carbonylation catalyst system comprising a rhodium catalyst and a co-catalyst (lithium iodide and methyl iodide), and a finite amount of water.

The process comprises a reaction system (reactor) 1 for carrying out the above-mentioned carbonylation reaction of methanol; a distillation column (or catalyst-separating column) 8 for separating mainly a higher boiling point fraction or stream (or higher bp fraction or stream) containing a metal catalyst component (or higher boiling point component or a higher bp component) [e.g., the rhodium catalyst and lithium iodide] from a reaction mixture (reaction solution) containing acetic acid generated by the reaction; a first distillation column 11 for removing mainly at least part of a lower bp component such as methyl iodide, methyl acetate and/or acetaldehyde from an acetic acid fraction or stream (lower bp fraction or stream) fed from the catalyst-separating column 8; a second distillation column 15 for separating mainly at least part of higher bp components (higher bp impurities) such as water and propionic acid from a side stream (acetic acid stream) withdrawn (or taken) by side cut in the first distillation column 11; a halide-removing column (iodide-removing column) 19 for removing an iodide such as an alkyl iodide from an acetic acid stream withdrawn by side cut in the second distillation column 15; and a condenser 21 for condensing the lower boiling point component from the first distillation column 11 to discharge a gaseous component and to recycle a liquid component to the first distillation column 11 and/or the reactor 1.

More specifically, to the reactor 1, methanol as a liquid component is continuously fed at a predetermined rate via a feed line 4 and carbon monoxide as a gaseous reactant is continuously fed via a feed line 5. Moreover, to the reactor 1, a catalyst mixture (catalyst solution) containing a carbonylation catalyst system (a catalyst system comprising a main catalyst component such as a rhodium catalyst, and a co-catalyst (e.g., lithium iodide, and methyl iodide)) and water may be fed through a feed line 6. Further, a fraction or stream (e.g., in the form of liquid) containing a lower bp fraction and/or a higher bp fraction from the succeeding step(s) (e.g., the catalyst-separating column 8, the first and second distillation columns 11 and 15, and the condenser 21) may be fed to the reactor 1 through the feed line 6. Then, inside the reactor 1, a liquid-phase reaction system containing the reactant and the higher bp component such as the metal catalyst component (e.g., rhodium catalyst, and lithium iodide) is in equilibrium with a vapor-phase system comprising carbon monoxide, as well as hydrogen, methane and carbon dioxide, and a vaporized lower bp component (e.g., methyl iodide, and acetic acid and methyl acetate) generated by the reaction, and a carbonylation reaction of methanol proceeds under stirring by a stirrer 2 or other means. In order to maintain the inner pressure of the reactor 1 (e.g., reaction pressure, and carbon monoxide partial pressure, hydrogen partial pressure) at a certain degree, part of a vapor may be withdrawn from the overhead of the reactor 1 through a discharge line 3, and discharged (removed off) (not shown). The vapor withdrawn from the reactor 1 may be further cooled by a heat exchanger E1 to form a liquid component (including acetic acid, methyl acetate, methyl iodide, acetaldehyde, water, and others) and a gaseous component (including carbon monoxide, hydrogen, and others), and the formed liquid component may be recycled to the reactor 1 through a recycle line 3a, or the formed gaseous component (waste gas) may be discharged through a discharge line 3b.

Incidentally, to the reactor 1, if necessary, hydrogen may be fed in order to enhance the catalytic activity. The hydrogen may be fed together with carbon monoxide through the feed line 5, or separately fed through another feed line (not shown). Moreover, since the reaction system is an exothermic reaction system that accompanies heat generation, the reactor 1 may comprise a heat-removing unit or cooling unit (e.g., jacket) for controlling a reaction temperature.

Components contained in the reaction mixture (crude reaction solution) generated in the reactor 1 may include acetic acid, hydrogen iodide, a lower bp component or lower bp impurities having a boiling point lower than that of acetic acid (e.g., methyl iodide as a co-catalyst, methyl acetate as a reaction product of acetic acid with methanol, and acetaldehyde, a higher iodide (such as hexyl iodide and decyl iodide) as by-products), and a higher bp component or higher bp impurities having a boiling point higher than that of acetic acid [a metal catalyst component (a rhodium catalyst, and lithium iodide as a co-catalyst), propionic acid, and water].

For separating mainly the higher bp component such as the metal catalyst component from the reaction mixture, part of the reaction mixture is continuously withdrawn from the reactor 1, and is introduced or fed to the distillation column (catalyst-separating column) 8 through a feed line 7.

Then, in the catalyst-separating column 8, from the reaction mixture, a higher bp fraction (mainly containing a metal catalyst component, e.g., a rhodium catalyst, lithium iodide, and others), and a lower bp fraction (mainly containing acetic acid which is a product and also functions as a reaction solvent, methyl acetate, methyl iodide, water, hydrogen iodide, and others) are separated, and the higher bp fraction is withdrawn from the bottom of the column through a bottom line 10, and the lower bp fraction (acetic acid stream) is withdrawn from the overhead or upper part of the catalyst-separating column 8 through a feed line 9 to feed or introduce into the first distillation column 11 through at least one of feed lines 9a and 9b. Incidentally, in the higher bp fraction, the metal catalyst component, and in addition methyl iodide, methyl acetate, hydrogen iodide, water, acetic acid, and others, which remain without evaporation are also contained. Incidentally, by making (keeping) the inner temperature and/or pressure of the catalyst-separating column 8 lower than those of the reactor 1, further generation of by-products or deterioration of the catalytic activity may be inhibited.

Incidentally, in the viewpoint of the separation efficiency of methyl iodide, it is advantageous to feed the acetic acid stream to the first distillation column 11 through a feed line 9a. Moreover, when the concentration of the water in the acetic acid stream is higher than 3% by weight, in the light of the separation efficiency of hydrogen iodide, it is advantageous to feed the acetic acid stream to the first distillation column 11 through a feed line 9b.

In the first distillation column 11, usually, a lower bp fraction (a first lower bp fraction) containing part of the lower bp component (containing methyl iodide, methyl acetate, acetaldehyde, water, and others) is separated (or removed) from the overhead or upper part of the column through a line 13, and a higher bp fraction (a first higher bp fraction) containing the higher bp component (e.g., water, and propionic acid) is separated (or removed) from the bottom or lower part of the column through a bottom line 14. Then, the side stream (acetic acid stream) mainly containing acetic acid is withdrawn from the first distillation column 11 by side cut through a feed line 12, and is fed or introduced into the second distillation column 15.

Hydrogen iodide is existence in the first distillation column 11. In the present invention, to prevent a purified acetic acid stream from contamination with hydrogen iodide or avoid condensation of hydrogen iodide in the distillation column 11, (i) water, (ii) methanol and/or methyl acetate (hereinafter, sometimes referred to as a component (A) or a first component (A)), or (iii) water and the component (A) is fed to the first distillation column 11 from at least one of upper and lower positions relative to a drawing port (side stream port) for conducting side cut of the acetic acid stream to convert the hydrogen iodide to a lower bp component (e.g., methyl iodide), and is separated from the overhead or upper part of the distillation column 11. The first component (A) and/or water may be, for example, fed through feed ports S1a, S1b and/or S1c, which may be located in any of upper and lower positions relative to the side stream port. In the case of feeding the first component (A) alone, usually the first component (A) is fed from a lower position relative to the side stream port.

The lower bp fraction withdrawn from the overhead or upper part of the first distillation column 11 contains acetic acid and others, and is fed to the condenser 21 through the line 13. In the condenser 21, the lower bp fraction is condensed to separate a gaseous component mainly containing carbon monoxide, hydrogen and others, and a liquid component containing methyl iodide, methyl acetate, acetic acid, acetaldehyde and others. The gaseous component separated in the condenser 21 is discharged through a discharge line 22, and if necessary, is recycled to the reaction system 1 through the feed line 5 or without through the feed line 5 (not shown). The liquid component separated in the condenser 21 is separated into an aqueous phase and an oily phase, and the aqueous phase and the oily phase are discharged through discharge lines 24 and 23, respectively. The oily phase discharged through the discharge line 23 is rich in methyl iodide as a co-catalyst, and may be recycled to the reaction system 1 through a recycle line 25. The aqueous phase discharged through the discharge line 24 is rich in methyl acetate, acetic acid, acetaldehyde and others, and may be recycled to the first distillation column 11 through a recycle line 24a or may be recycled to the reaction system through recycle lines 24b and 25. The recycling of the oily phase or the aqueous phase to the reactor may be carried out via the feed line 6 (not shown). The discharge stream from at least one of the line (overhead) 13 and the discharge lines 23 and 24 may be further subjected to an aldehyde-separating step (column) (not shown) to separate or remove an aldehyde.

The higher bp fraction discharged from the bottom of the first distillation column 11 contains the higher bp component, as well as the lower bp component and acetic acid which remain without evaporation, and others, and may be recycled to the reaction system 1. The higher bp fraction may be, if necessary, joined to (or combined to) a recycle line of the succeeding step (e.g., the second distillation column, the aldehyde-separating column, and the condenser) (in the embodiment of FIG. 1, a recycle line 25 for recycling a liquid component from the condenser 21) for recycling to the reaction system 1.

In the acetic acid stream which is obtained by side cut from the first distillation column 11 and is fed to the second distillation column 15 through the feed line 12, at least part of the lower bp component (e.g., methyl iodide, methyl acetate, and acetaldehyde) remaining in the acetic acid stream, and at least part of the higher bp component (e.g., propionic acid, and water) are further separated in the second distillation column 15, and an acetic acid stream having a higher purity is withdrawn as a side stream. In the second distillation column 15, a fraction (lower bp fraction, second lower bp fraction) containing the lower bp component is discharged from the overhead or upper part of the column through a discharge line 17, and a fraction (higher bp fraction, second higher bp fraction) containing the higher bp component is discharged from the bottom of the column or lower part of the column through a bottom line 18, and a side stream (acetic acid stream) rich in acetic acid is distilled by side cut through a line 16. If necessary, the lower bp fraction discharged from the overhead or upper part of the column may be recycled to the second distillation column 15 and/or the reaction system 1 (not shown). Moreover, if necessary, the higher bp fraction discharged from the bottom or lower part of the column may be recycled to the reaction system 1 (not shown).

In order to lower the concentration of the hydrogen iodide contained in the acetic acid stream withdrawn by side cut and to avoid condensation of the hydrogen iodide in the distillation column 15, usually, at least one member (hereinafter, sometimes referred to as a component (B) or a second component (B)) selected from the group consisting of (b-1) methanol, (b-2) methyl acetate, (b-3) an alkali metal hydroxide such as potassium hydroxide, (b-4) an alkali metal acetate such as potassium acetate and (b-5) a hypophosphorous acid may be fed to the second distillation column 15 from at least any one of upper and lower positions relative to the drawing port (side stream port) for side cut of the acetic acid stream. The second component (B) may be fed, for example, from a feed port (e.g., feed ports S2a and/or S2b) which is located in at least any one of upper and lower positions relative to the side stream port. In the case where the methanol and/or methyl acetate is fed to the second distillation column 15, as is the case with the first distillation column 11, the methanol and/or methyl acetate is converted to a lower bp component (e.g., methyl iodide) by a reaction with hydrogen iodide, and can be separated or discharged as a lower bp fraction from the overhead or upper part of the distillation column 15. Incidentally, in the case where the alkali metal hydroxide (usually, an aqueous solution thereof) is fed from a lower position relative to the side stream port (e.g., from the feed port S2b), the amount of the hydrogen iodide to be contaminated in the side cut acetic acid stream can be reduced to a trace amount. Moreover, in the case where the alkali metal hydroxide (usually, an aqueous solution) is fed from an upper position relative to the side stream port (e.g., from the feed port S2a), the amount of the hydrogen iodide to be contaminated in the side cut acetic acid stream can be further reduced compared with the case of feeding the alkali metal hydroxide from the lower position.

The acetic acid stream obtained by side cut from the second distillation column 15 is introduced into a heat exchanger E2 through the line 16 for cooling, and further, is fed through a feed line 16a to the overhead or upper part of a halide (iodide)-removing column 19 equipped with an ion exchange resin therein, where the active group of the ion exchange resin is at least partly replaced or exchanged with Ag. Inside of the halide-removing column 19, along with falling of the acetic acid stream, the acetic acid stream is passed through the ion exchange resin with stepwise raising (elevating) the temperature of the acetic acid stream to remove an iodide such as an alkyl iodide, and a purified acetic acid is distilled from the bottom of the column through a line 20. Thus obtained acetic acid as a final product has an extremely low concentration of the hydrogen iodide because of feeding the first component (A) and/or water to the first distillation column 11, and further feeding the second component (B) to the second distillation column 15. Moreover, since the distillations are carried out at two steps, that is, the first and second distillation columns 11 and 15, the removal rates of the lower bp component (lower bp impurities) and the higher bp component (higher bp impurities) are considerably high. In addition, since the acetic acid stream is passed though the halide-removing column 19, contamination with a halide such as an alkyl iodide is remarkably reduced, and highly pure acetic acid is obtained. Moreover, since condensation of hydrogen iodide inside of the distillation column(s) is effectively inhibited, corrosion or degradation of the distillation(s) column can be also prevented.

Figure 2:
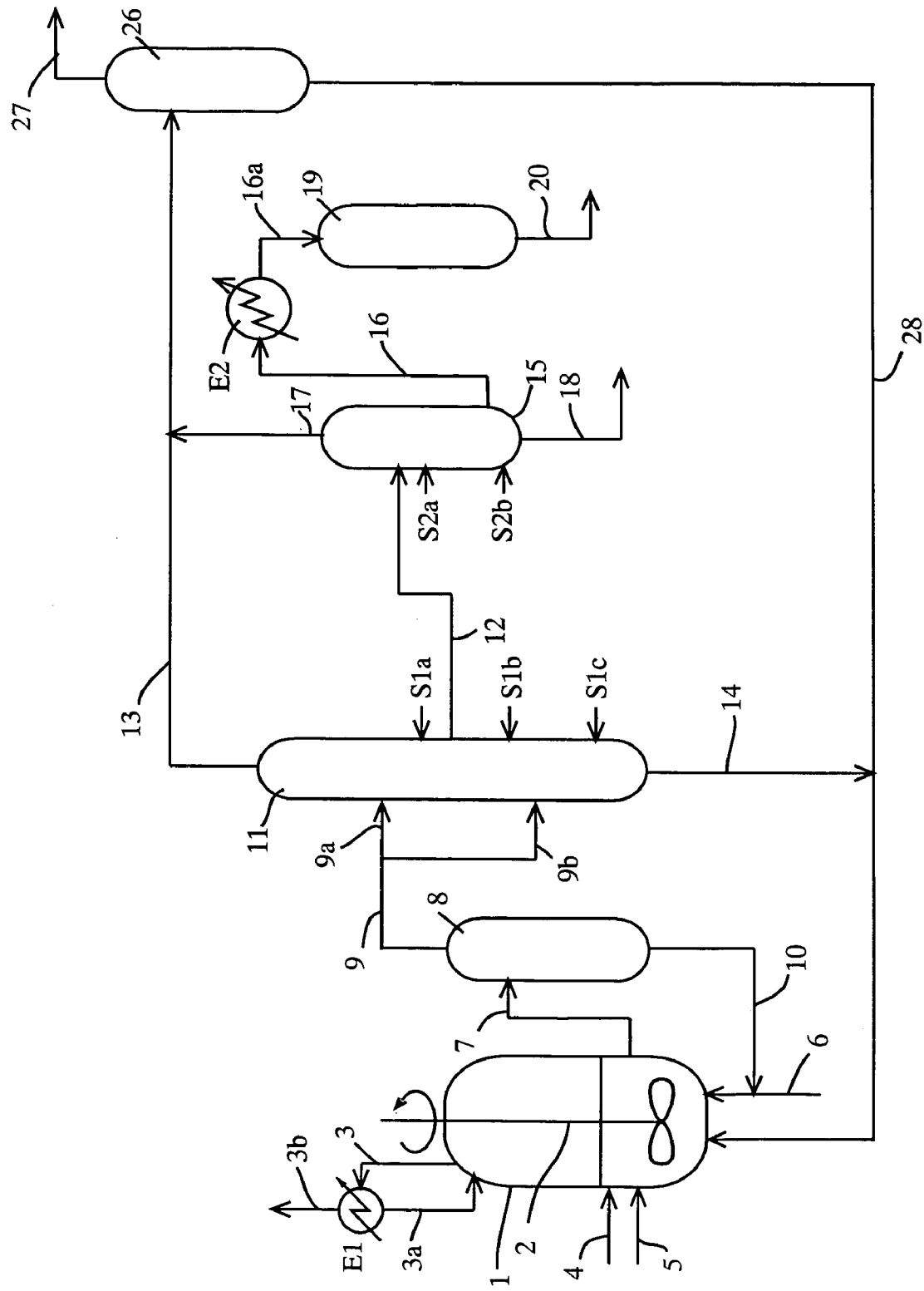
FIG. 2 is a flow diagram for illustrating another embodiment of a production process of a carboxylic acid of the present invention.

FIG. 2 is a flow diagram for explaining another embodiment of a production process of a carboxylic acid of the present invention. The embodiment of FIG. 2 corresponds to an example that, in the embodiment of FIG. 1, the lower bp fractions containing the lower bp components withdrawn from the first distillation column 11 and the second distillation column 15 are further fed to an aldehyde-separating column 26 to separate a lower bp fraction containing an aldehyde and a higher bp fraction for recycling the higher bp fraction to the reaction system 1. More specifically, in the embodiment of FIG. 2, the lower bp fraction containing the lower bp component withdrawn from the overhead or upper part of the first distillation column 11 is further fed to the aldehyde-separating column 26 through the line (feed line) 13, and the lower bp fraction containing the lower bp component withdrawn from the second distillation column 15 is joined to (combined to) the feed line 13 via the line 17, and both fractions are fed to the aldehyde-separating column 26. Then, in the aldehyde-separating column 26, the lower bp fraction containing the lower bp component such as acetaldehyde, carbon monoxide, or hydrogen, and the higher bp fraction containing the higher bp component such as methyl iodide, methyl acetate, water, or acetic acid are separated. The lower bp fraction is discharged from the overhead or upper part of the column through a discharge line 27, and the higher bp fraction is withdrawn from the bottom of the column through a bottom line (recycle line) 28. The higher bp fraction withdrawn from the bottom of the column may be recycled to the reaction system 1 through a recycle line 28. Incidentally, the lower bp fraction discharged from the discharge line 27 may be further treated by a conventional method, e.g., extraction, washing, or others, to increase the separation efficiency of the aldehyde.

Moreover, the higher bp fraction may be fed to the first distillation column 11 and/or the second distillation column 15 (not shown) to increase separability between acetic acid and water in the distillation column. Further, if necessary, the higher bp fraction from the aldehyde-separating column 26 may be introduced into a condenser (not shown) for condensation to separate an oily phase rich in methyl iodide, and an aqueous phase rich in methyl acetate, water and acetic acid. Then, in the same manner as the embodiment of FIG. 1, the oily phase may be recycled to the reaction system 1, or the aqueous phase may be recycled to any of the first distillation column 11, the second distillation column 15, and the reaction system 1. Incidentally, the higher bp fraction withdrawn from the bottom of the first distillation column 11 and/or the second distillation column 15 may be recycled to the reaction system 1 through the recycle line 28, or if necessary, may be recycled to the reaction system 1 through the feed line 6 (not shown).

Thus, in the embodiment of FIG. 2, since an aldehyde is removed by subjecting the lower bp fractions from the first and second distillation columns 11 and 15 to the aldehyde-separating column before recycling to the reaction system or the distillation column, circulation of the aldehyde by recycling in a continuous process can be inhibited. As a result, it can be drastically reduced to generate impurities (e.g., propionic acid, crotonaldehyde, 2-ethylcrotonaldehyde, hexyl iodide, and decyl iodide) as consecutive reaction products from the aldehyde. Incidentally, a step for feeding to aldehyde-separating column 26 the fraction (overhead) from the second distillation column discharged through the discharge line 17 may be omitted.

The production process of the present invention is applicable to a variety of carbonylation reactions of various alcohols or derivatives thereof without limiting the above-mentioned carbonylation of methanol.

(Reaction Step (Carbonylation Reaction System))

In the reaction system, an alcohol or a derivative thereof (e.g., a reactive derivative such as an ester, an ether, or a halide) is carbonylated with carbon monoxide. As the alcohol to be used in the carbonylation reaction, there may be exemplified an alcohol having "n" carbon atom(s), for example, an aliphatic alcohol [e.g., an alkanol (e.g., a $C_{1-10}$alkanol) such as methanol, ethanol, propanol, isopropanol, butanol, pentanol, or hexanol], an alicyclic alcohol [e.g., a cycloalkanol (e.g., a $C_{3-10}$cycloalkanol) such as cyclohexanol or cyclooctanol], an aromatic alcohol [an aryl alcohol (e.g., a $C_{6-10}$aryl alcohol (such as a phenol compound)) such as phenol; an aralkyl alcohol (e.g., a $C_{6-10}$aryl-$C_{1-4}$alkanol) such as benzyl alcohol or phenethyl alcohol], or others. The number "n" of carbon atoms is about 1 to 14, preferably about 1 to 10, and more preferably about 1 to 6. Among the foregoing alcohols, an aliphatic alcohol is preferred. The number "n" of carbon atoms in the aliphatic alcohol is, for example, about 1 to 6, preferably about 1 to 4, and particularly about 1 to 3.

Among the alcohol derivatives, as the ester, there may be exemplified an ester of a carboxylic acid to be formed with a raw alcohol, for example, a $C_{1-6}$alkyl ester of a $C_{2-6}$carboxylic acid such as methyl acetate or ethyl propionate, or others. As the ether, there may be exemplified an ether corresponding to the raw alcohol, for example, a di$C_{1-6}$alkyl ether such as methyl ether, ethyl ether, propyl ether, isopropyl ether or butyl ether, or the like. Moreover, as the halide, there may be used a halide corresponding to the alcohol, such as methyl iodide (e.g., an alkyl halide such as an alkyl iodide). Further, if necessary, as an alcohol, there may be used a polyhydric alcohol, for example, an alkylene glycol such as ethylene glycol, propylene glycol or butanediol, or a derivative thereof (e.g., an ester, a halide, an ether).

The alcohol or a derivative thereof may be used singly or in combination.

In the preferred liquid-phase reaction system, an alcohol having "n" carbon atom(s) as a liquid reactant, preferably a $C_{1-4}$alcohol or a derivative thereof (e.g., methanol, methyl acetate, methyl iodide, and dimethyl ether) may be used to obtain a carboxylic acid having "n+1" carbon atoms or a derivative thereof (e.g., a carboxylic anhydride). In particular, the following reaction system is preferred: a reaction system in which at least one member selected from the group consisting of methanol, methyl acetate, and dimethyl ether (particularly at least methanol) is allowed to react with carbon monoxide in the presence of a carbonylation catalyst system in a liquid-phase reaction system, to produce acetic acid or a derivative thereof.

Incidentally, as the alcohol or a derivative thereof, a fresh raw material may be directly or indirectly fed to the reaction system. Moreover, an alcohol or a derivative thereof withdrawn from a distillation step may be recycled and fed to the reaction system.

The catalyst system in the reaction system may comprise a carbonylation catalyst, and a co-catalyst or accelerator. As the carbonylation catalyst, there may be usually employed a catalyst having a high boiling point, e.g., a metal catalyst. As the metal catalyst, there may be exemplified a transition metal catalyst, in particular a metal catalyst containing a metal element of the Group 8 of the Periodic Table of Elements, for example, a cobalt catalyst, a rhodium catalyst, an iridium catalyst, or others. The catalyst may be a simple metal, or may be used in the form of a metal oxide (including a complex metal oxide), an metal hydroxide, a metal halide (e.g., a chloride, a bromide, an iodide), a metal carboxylate (e.g., an acetate), a metal salt of an inorganic acid (e.g., a sulfate, a nitrate, a phosphate), a metal complex or others. Such a metal catalyst may be used singly or in combination.

The preferred metal catalyst includes a rhodium catalyst and an iridium catalyst (in particular a rhodium catalyst). Further, it is preferred to use the metal catalyst in the form dissolvable in a reaction solution. Incidentally, rhodium usually exists as a complex in the reaction solution, and in the case using a rhodium catalyst, the catalyst is not particularly limited as far as the catalyst can change into a complex in the reaction solution, and may be used in various forms. As such a rhodium catalyst, a rhodium halide (such as bromide or iodide) is particularly preferred. Moreover, the catalyst may be stabilized in the reaction solution by adding a salt of a halide (e.g., a salt of an iodide) and/or water thereto.

The concentration of the catalyst is, for example, about 10 to 5,000 ppm, preferably about 100 to 4,000 ppm, more preferably about 300 to 3,000 ppm, and particularly about 500 to 2,000 ppm on the basis of weight relative to the total amount of the liquid-phase system. In the case where the concentration of the catalyst is too high, due to the change of the catalyst (e.g., a rhodium catalyst) into an insolvable component (e.g., a rhodium halide such as rhodium iodide) and the precipitation thereof, there is a possibility to reduce the reaction efficiency and productivity.

As the co-catalyst or accelerator constituting the catalyst system, there may be used various halides, for example, alkali metal halides (e.g., an iodide such as lithium iodide, potassium iodide, or sodium iodide; a bromide such as lithium bromide, potassium bromide or sodium bromide), a hydrogen halide (e.g., hydrogen iodide, hydrogen bromide), an alkyl halide [an alkyl halide (a $C_{1-10}$ alkyl halide, preferably a $C_{1-4}$ alkyl halide) corresponding to a raw alcohol, for example a $C_{1-10}$ alkyl iodide (e.g., a $C_{1-4}$ alkyl iodide) such as methyl iodide, ethyl iodide or propyl iodide, a bromide corresponding to these alkyl iodides (e.g., methyl bromide, propyl bromide), or a chloride corresponding to these alkyl iodides (e.g., methyl chloride)]. Incidentally, the alkali metal halide (particularly an iodide) also functions as a stabilizer of the carbonylation catalyst (e.g., a rhodium catalyst). These co-catalysts or accelerators may be used singly or in combination. In particular, it is preferred to use an alkali metal halide (in particular an alkali metal iodide) in combination with an alkyl halide (in particular an alkyl iodide) and/or a hydrogen halide. The preferred catalyst system includes a catalyst system comprising a metal catalyst component (e.g., a rhodium catalyst, and an alkali metal halide) and an alkyl halide.

The content of the co-catalyst or accelerator may be, for example, about 0.1 to 40% by weight, preferably about 0.5 to 30% by weight, and more preferably about 1 to 25% by weight relative to the whole liquid-phase system. More specifically, in a production of a carboxylic acid by the foregoing carbonylation reaction of an alcohol, the content of the alkyl halide such as methyl iodide may be, for example, about 1 to 25% by weight, preferably about 5 to 20% by weight, and more preferably about 5 to 15% by weight relative to the whole liquid-phase system. Incidentally, the higher the concentration (content) of the alkyl halide is, the more the reaction is accelerated (promoted). The economically advantageous concentration can be suitably selected in consideration of recovery of the alkyl halide, the size or scale of the facility in which the step for circulating the recovered alkyl halide into the reactor is carried out, the amount of energy necessary to the recovery or circulation, and others. Moreover, the content of the alkali metal halide such as lithium iodide may be, for example, about 0.1 to 40% by weight, preferably about 0.5 to 35% by weight, and more preferably about 1 to 30% by weight relative to the whole liquid-phase system.

Incidentally, in the reaction system, a carboxylic acid ester (in particular an ester of a carboxylic acid with an alcohol, such as methyl acetate) may be included in a proportion of about 0.1 to 20% by weight, and preferably about 0.5 to 15% by weight relative to the whole liquid-phase system. Incidentally, in the reaction solution, there exists usually about 0.5 to 10% by weight of the carboxylic acid ester due to equilibrium of the alcohol as the raw material and the product carboxylic acid.

Carbon monoxide for feeding to the reaction system may be used as a pure gas, or may be used as a gas diluted with an inert gas (e.g., nitrogen, helium, carbon dioxide). Moreover, an exhausted gas component containing carbon monoxide obtained from succeeding steps (e.g., a distillation step (distillation column), a condenser, and an aldehyde-separating column) may be recycled to the reaction system. The carbon monoxide partial pressure in the reaction system may be, for example, about 0.9 to 3 MPa (e.g., 0.9 to 2 MPa), preferably about 1 to 2.5 MPa (e.g., about 1.15 to 2.5 MPa), and more preferably about 1.15 to 2 MPa (e.g., 1.18 to 2 MPa) as an absolute pressure. Incidentally, not limited to the embodiments of FIGS. 1 and 2, carbon monoxide may be fed from the lower part of the reactor by sparging.

In the carbonylation reaction, hydrogen is formed (or generated) by a shift reaction between carbon monoxide and water. Additionally, hydrogen may be fed to the reaction system. The hydrogen may be fed as a mixed gas with carbon monoxide as a raw material to the reaction system. Moreover, the hydrogen may be fed to the reaction system by recycling a gaseous component (including hydrogen, carbon monoxide, and others) exhausted in the succeeding distillation step (distillation column), if necessary after suitably purifying the gaseous component. The hydrogen partial pressure in the reaction system may be, for example, about 0.5 to 200 kPa, preferably about 1 to 150 kPa, and more preferably about 5 to 100 kPa (e.g., 10 to 50 kPa) as an absolute pressure.

Incidentally, the carbon monoxide partial pressure or hydrogen partial pressure in the reaction system may be adjusted, for example, by suitably adjusting the amount of the carbon monoxide and hydrogen fed and/or recycled to the reaction system, the amount of raw substances (e.g., methanol) fed to the reaction system, the reaction temperature, the reaction pressure, and others.

In the carbonylation reaction, the reaction temperature may be, for example, about 100 to 250° C., preferably about 150 to 220° C., and more preferably about 170 to 210° C. Moreover, the reaction pressure in terms of gauge pressure may be, for example, about 1 to 5 MPa, preferably about 1.5 to 4 MPa, and more preferably about 2 to 3.5 MPa.

The reaction may be carried out in the presence or absence of a solvent. The reaction solvent is not limited to a specific one as far as the reactivity, or the separation or purification efficiency does not decrease, and a variety of solvents may be used. In usual cases, carboxylic acids (e.g., acetic acid) as a product may be practically utilized as a solvent.

The concentration of water in the reaction system is not limited to a specific one, and may be a low concentration. The concentration of water in the reaction system is for example about 0.1 to 10% by weight, preferably about 0.1 to 7% by weight, and more preferably about 0.1 to 5% by weight relative to the total amount of liquid-phase of the reaction system. Moreover, in order to prevent the reduction of the reaction rate or to avoid destabilization of the metal catalyst, if necessary, into the reaction system there may be added a compound which is capable of forming a salt of an iodide salt in the reaction system, for example, an alkali metal halide (e.g., the above-exemplified alkali metal halides), a quaternary ammonium salt or quaternary phosphonium salt of an alkali metal. Among these components, from the viewpoint of solubility, it is preferred to use an alkali metal iodide, particularly lithium iodide.

In the foregoing carbonylation reaction, a carboxylic acid having "n+1" carbon atoms (e.g., acetic acid) corresponding to an alcohol having "n" carbon atom(s) (e.g., methanol) is formed together with an ester of the formed carboxylic acid with the alcohol (e.g., methyl acetate), water generated with the esterification reaction, in addition an aldehyde having "n+1" carbon atoms (e.g., acetaldehyde) corresponding to the alcohol, a carboxylic acid having "n+2" carbon atoms (e.g., propionic acid), and others.

Incidentally, in the reaction system, generation of aldehydes may be depressed or inhibited by removing the aldehyde in the recycling stream from the succeeding steps (e.g., distillation column), or by modifying the reaction conditions, for example, reducing the proportion of the co-catalyst such as an alkyl iodide and/or the hydrogen partial pressure. Moreover, the generation of hydrogen in the reaction system may be depressed or inhibited by adjusting the water concentration.

The space time yield of the objective carboxylic acid in the reaction system may be, for example, about 5 mol/Lh to 50 mol/Lh, preferably about 8 mol/Lh to 40 mol/Lh, and more preferably about 10 mol/Lh to 30 mol/Lh.

(Catalyst-Separating Step)

In the catalyst-separating step (catalyst-separating column), from the reaction mixture fed from the reaction step, a higher bp fraction (or stream) containing at least a higher bp catalyst component (a metal catalyst component, e.g., a carbonylation catalyst such as a rhodium catalyst, and an alkali metal halide) is separated as a liquid (component), and a lower bp fraction (carboxylic acid stream) containing a carboxylic acid is separated as a vapor (component).

The separation of the metal catalyst component may be conducted by a conventional separation method or separation apparatus, and may be usually carried out with the use of a distillation column (e.g., a plate column, a packed column, a flash distillation column). Moreover, the metal catalyst component may be separated by means of distillation in combination with a mist- or solid-collecting method which is widely used in industrial application.

In the catalyst-separating step, the reaction mixture may be separated into the vapor component and the liquid component with or without heating. For example, when flash distillation is utilized, in adiabatic flash, the reaction mixture may be separated into the vapor component and the liquid component without heating and with reduced pressure, and in thermostatic flash, the reaction mixture may be separated into the vapor component and the liquid component with heating and reduced pressure. The reaction mixture may be separated into the vapor component and the liquid component by combining these flash conditions. These flash distillation steps may be carried out, for example, at a temperature of about 80 to 200° C. under a pressure (absolute pressure) of about 50 to 1,000 kPa (e.g., about 100 to 1,000 kPa), preferably about 100 to 500 kPa, and more preferably about 100 to 300 kPa.

The catalyst-separating step may be composed of a single step, or may be composed of a plurality of steps in combination. The higher bp catalyst component (metal catalyst component) separated by such a step is usually recycled to the reaction system.

The lower bp fraction (carboxylic acid stream) separated in the catalyst-separating column contains a product carboxylic acid (e.g., acetic acid), in addition, a co-catalyst such as hydrogen iodide or methyl iodide, an ester of the product carboxylic acid with a raw alcohol (e.g., methyl acetate), water, a small amount of by-product(s) (e.g., an aldehyde such as acetaldehyde, and a carboxylic acid having "n+2" carbon atoms such as propionic acid). In the present invention, the purified carboxylic acid may be produced by distilling the carboxylic acid stream in the first distillation column and the second distillation column.

(First Distillation Column)

In the first distillation column, a lower bp fraction (a first lower bp fraction) containing at least part of an lower bp component [e.g., a halogenated hydrocarbon such as an alkyl halide, an alkyl ester of a carboxylic acid (e.g., a carboxylic acid having "n+1" carbon atoms) (e.g., an ester with an alcohol having "n" carbon atom(s)), an aldehyde having "n+1" carbon atoms] and higher bp fraction (a first higher bp fraction) containing at least part of a higher bp component (e.g., a carboxylic acid having "n+2" carbon atoms, and water) (bottoms) are separated from the carboxylic acid stream (e.g., acetic acid stream) fed from the catalyst-separating column; and a fraction (side stream) containing at least a carboxylic acid having "n+1" carbon atoms is withdrawn by side cut. Incidentally, in usual cases, the lower bp component(s) and water are mainly removed (separated) from the first distillation column.

As mentioned above, the carboxylic acid stream fed to the first distillation column is not limited to a carboxylic acid stream obtained by removing the metal catalyst component from the reaction mixture of the reaction system. The carboxylic acid stream may be a one containing at least a carboxylic acid having "n+1" carbon atoms, a hydrogen halide, the lower bp component, the higher bp component, and others; or simply may be a mixture of these components. Moreover, the reaction mixture from the reaction system may be directly fed as the carboxylic acid stream to the first distillation column, and the higher bp fraction containing the metal catalyst component may be withdrawn from the bottom of the first distillation column.

The feed port for feeding the carboxylic acid stream from the catalyst-separating column is not limited to a specific one, for example, may be any one of upper part, middle part, or lower part of the first distillation column. Moreover, in the first distillation column, the carboxylic acid stream from the catalyst-separating column may be fed from either upper or lower position relative to a side stream port for conducting side cut of the objective carboxylic acid. The feeding of the carboxylic acid stream from the upper position relative to the side stream port realizes enhancement the separation efficiency of an alkyl halide or others. The feeding of the carboxylic acid stream from the lower position relative to the side stream port realizes (in particular in the case where the water concentration in the carboxylic acid stream is not lower than 3% by weight) significantly enhancement the removal efficiency of the hydrogen halide.

Moreover, the position of the side stream port for side cut of the objective carboxylic acid may be any one of upper part, middle part, or lower part of the first distillation column. In usual cases, the position of the side stream port is preferably middle part or lower part in the first distillation column. As mentioned above, since in the first distillation column, the objective carboxylic acid stream is taken out by side cut not by overhead, the objective carboxylic acid stream is effectively prevented from recontamination of the hydrogen iodide generated by hydrolysis of an alkyl iodide.

According to the present invention, water and/or at least one component (first component) (A) selected from the group consisting of an alcohol having "n" carbon atom(s) (e.g., methanol) corresponding to an objective carboxylic acid having "n+1" carbon atoms and an ester (e.g., methyl acetate) of the alcohol with the objective carboxylic acid is fed to at least the first distillation column. By feeding such a component to the first distillation column, hydrogen halide (e.g., hydrogen iodide) in the distillation column can be converted to a lower bp component such as an alkyl halide having "n" carbon atom(s), and can be efficiently separated out of the system from the overhead or upper part of the column. Accordingly, contamination of the hydrogen halide in the objective carboxylic acid, or corrosion of the distillation column due to condensation of the hydrogen halide inside of the distillation column is effectively inhibited. Incidentally, feeding of the ester (e.g., methyl acetate) to the distillation column can also improve separability of water from the objective carboxylic acid, since the ester forms an azeotropic system with water.

As the first distillation column, there may be used, for example, a conventional distillation column, e.g., a plate column, a packed column, a flash distillation column, and others. Incidentally, the material of the distillation column is not limited to a specific one, and a material of a glass, a metal, a ceramic, or others is usable. In usual, a distillation column made of a metal is used practically. Incidentally, in the case of using a distillation column made of a material capable of shielding light, such as a metal, generation of a free halogen such as free iodine can be also inhibited.

The feeding position of the first component (A) and/or water to the first distillation column is not limited to a specific one, and may be any position in the height (or longitudinal) direction of the distillation column. The above component(s) is usually fed from at least one position selected from the upper and lower positions relative to the side stream port in which the objective carboxylic acid stream is obtained by side cut in many cases. Incidentally, in the case of feeding the first component (A) alone (including the case of feeding the first component (A) as a carboxylic acid solution), the first component (A) is fed from the lower position relative to the side stream port.

To the first distillation column, at least one member selected from the first components (e.g., methanol, methyl acetate) may be fed alone. The first component (A) may be fed with a product carboxylic acid (e.g., acetic acid), for example, as a carboxylic acid solution thereof. In the case of feeding the first component (A) and water, each of water and at least one member selected from the first components (e.g., methanol, and methyl acetate) may be separately fed; or the first component (A) and water may be fed as a mixture (e.g., aqueous solution). The water may be fed alone to the first distillation column, or may be fed with a product carboxylic acid. Feeding water to the first distillation column develops (forms) a zone having a high water concentration in the distillation column, and causes condensation (concentration) of hydrogen halide in the zone. Moreover, feeding of water with the first component (A) ensures to convert hydrogen halide into the lower bp component efficiently. In the case of feeding the first component (A) from the lower position relative to the side stream port, a hydrogen halide can be efficiently removed. Moreover, the removal rate or degree of the hydrogen halide is further enhanced by (i) feeding water, or both the first component (A) (particularly an alcohol) and water from the upper position relative to the side stream port, or (ii) feeding at least water [in particular, water and the first component (A) (in particular, at least an alcohol, i.e., an alcohol, or an alcohol and an ester)] from the upper position relative to the side stream port, and feeding the first component (A) (particularly an alcohol) from the lower position relative to the side stream port. In particular, in the case of feeding a carboxylic acid stream (e.g., a carboxylic acid stream from the catalyst-separating column) to the first distillation column from the upper position relative to the side stream port, such an effect is significant. Incidentally, feeding water to the first distillation column accelerates (promotes) dissociation or ionization of the hydrogen halide (e.g., hydrogen iodide), and the dissociated or ionized hydrogen halide becomes more reactive to the first component (A). As a result, the removal rate or degree of the hydrogen halide is improved or enhanced. Accordingly, it is preferred to add (or feed) both water and the first component (A) to the first distillation column. Incidentally, the number of feed ports feeding the first component (A) and/or water is not limited to a specific one, and the above component(s) may be fed from either one feed port or a plurality of feed ports.

In the present invention, since the first component (A) and/or water is(are) fed to the first distillation column, the concentration of the hydrogen halide in the side stream (objective carboxylic acid stream) from the first distillation column can be remarkably reduced. The concentration of the hydrogen halide in the objective carboxylic acid stream may be, depending on the concentration of the hydrogen halide in the carboxylic acid stream fed to the first distillation column, for example, not higher than 25 ppm (e.g., about 0 to 25 ppm), preferably not higher than 20 ppm (e.g., finite or limited concentration to about 20 ppm), more preferably not higher than 15 ppm, and particularly not higher than 10 ppm.

The feed proportions of the first component (A) (the alcohol and an ester thereof) and that of the water may be, respectively, for example, (i) about 1 to 10,000 mol, preferably about 10 to 6,000 mol (e.g., 100 to 5,000 mol), and more preferably about 500 to 5,000 mol relative to 1 mol of the hydrogen halide contained in the carboxylic acid stream (the carboxylic acid stream fed to the first distillation column). Moreover, the feed proportion of the first component (A) and/or the water may be (ii) about 0.02 to 50% by mol, preferably about 0.1 to 30% by mol (e.g., 1 to 25% by mol), and more preferably about 1.5 to 20% by mol either relative to the total amount of the carboxylic acid having "n+1" carbon atoms contained in the carboxylic acid stream (the carboxylic acid stream fed to the first distillation column) or relative to the total amount of the alcohol fed to the reaction system. The feed proportions may satisfy at least one of the above range of either (i) or (ii), and may usually satisfy both ranges of (i) and (ii).

Moreover, at least one component selected from the group consisting of an alkali metal hydroxide (such as sodium hydroxide or potassium hydroxide), an alkali metal acetate (such as potassium acetate), and a hypophosphorous acid may be fed to the first distillation column so as to further enhance the separation efficiency of the hydrogen halide. These components are usually fed as an aqueous solution in many cases. In the case of feeding these components as the aqueous solution, the proportion of water may be suitably selected within the range in which the total amount of water fed to the first distillation column does not exceed the range of the above feed proportion. Incidentally, instead of the water, acetic acid, methanol and/or methyl acetate may be used as a solvent. The conditions such as a feeding amount (feed proportion), a feeding position, and others may be selected from the ranges described in the paragraph of the below-mentioned second distillation column.

The distillation temperature and pressure in the first distillation column may be suitably selected depending on the condition such as the species of the objective carboxylic acid and the distillation column, or the main subject (target) for removal selected from the lower bp component and the higher bp component. For example, in the case of purifying acetic acid in the plate column, the inner pressure (usually, overhead pressure) of the column may be about 0.01 to 1 MPa, preferably about 0.01 to 0.7 MPa, and more preferably about 0.05 to 0.5 MPa in terms of gauge pressure. Incidentally, distillation under an applied pressure can prevent the distillation column from contamination of air, as well as can inhibit generation of a free halogen (free iodine). Incidentally, due to generation of a free halogen such as free iodine, the objective carboxylic acid sometimes turns dark yellow or brown. Accordingly, a hypophosphorous acid or others may be suitably fed (e.g., in the initial step of the process operation) to convert the free halogen to a hydrogen halide.

Moreover, in the first distillation column, the inner temperature of the column (usually overhead temperature) may be adjusted by adjusting the inner pressure of the column, and may be, for example, about 20 to 180° C., preferably about 50 to 150° C., and more preferably about 100 to 140° C.

Moreover, in the case of a plate column, the theoretical number of plates is not particularly limited to a specific one, and, depending on the species of the component to be separated, is about 5 to 50, preferably about 7 to 35, and more preferably about 8 to 30. Further, in order to separate an aldehyde highly (or with a high precision) in the first distillation column, the theoretical number of plates may be about 10 to 80, preferably about 20 to 60, and more preferably about 25 to 50.

In the first distillation column, the reflux ratio may for example be selected from about 0.5 to 3,000, and preferably about 0.8 to 2,000 depending on the above-mentioned theoretical number of plates, or may be reduced by increasing the theoretical number of plates. Incidentally, the lower bp fraction obtained by removing the higher bp catalyst component from the separation step of the catalyst component is not necessarily subjected to reflux, and may be fed from the overhead of the first distillation column.

Since the lower bp fraction separated from the first distillation column contains an alkyl halide, an alkyl ester of a carboxylic acid, water and others, the lower bp fraction may be recycled to the reaction system and/or the first distillation column. Incidentally, the lower bp fraction withdrawn from the first distillation column is not necessary to condensate with a condenser as shown in the embodiment of FIG. 1 for recycling. The withdrawn lower bp fraction may be directly recycled, or after removing off an off gas component such as carbon monoxide or hydrogen by simply cooling the withdrawn lower bp fraction, the remaining liquid component may be recycled. Further, among lower bp components in the lower bp fraction, an aldehyde deteriorates the quality of the carboxylic acid as a final product. Therefore, if necessary, after removing the aldehyde (e.g., after removing the aldehyde by subjecting the fraction containing the lower bp impurities to the aldehyde separation step (aldehyde-separating column)), the remaining component (s) may be recycled to the reaction system and/or the first distillation column. In the case of condensing the lower bp fraction with the condenser for recycling, it is not necessary needed that the liquid component is divided into two phases, an aqueous phase and an oily phase, to separately recycle the two phases, as shown in the embodiment of FIG. 1. The liquid component may be recycled to the reaction system, the first and/or the second distillation column, without dividing into the two phases. Moreover, in the case of separating the liquid component into two phases, either one of the phases may be recycled to the reaction system and/or the distillation columns.

The higher bp fraction (bottom solution) separated in the first distillation column contains water, a carboxylic acid having "n+2" carbon atoms, an entrained rhodium catalyst, lithium iodide, in addition, the objective carboxylic acid remaining without being evaporated, the lower bp impurities, and others. Therefore, if necessary, the higher bp fraction may be recycled to the reaction system. Incidentally, prior to recycling, the carboxylic acid having "n+2" carbon atoms which deteriorates the quality of the objective carboxylic acid may be removed off. Moreover, the bottom solution is not necessary to be combined with the recycle stream from the succeeding steps, and may be directly recycled to the reaction system. The bottom solution, if necessary, for recycling to the reaction system, may be joined to a feed line for feeding a raw material or a catalyst to the reaction system.

Incidentally, if necessary, separability of water from a carboxylic acid such as acetic acid may be improved or enhanced by adding to the first distillation column a component which is capable of azeotropic with water, for example, an alkyl iodide (e.g., methyl iodide).

(Second Distillation Column)

In the second distillation column, a hydrogen halide, a lower bp component, and a higher bp component which remain without being separated in the first distillation column are removed with further high precision. The feeding portion of the carboxylic acid stream from the first distillation column is not limited to a specific one, and may be located, for example, at any of upper, middle, or lower part of the second distillation column. In usual cases, it is preferred to provide the carboxylic acid stream to a middle part of the column.

As the second distillation column, there may be used a conventional distillation column, for example, a plate column, a packed column, a flash distillation column, and other columns. Moreover, the inner temperature of the column, the inner pressure of the column, the theoretical number of plates, and the reflux ratio in the second distillation column may be selected depending on the species of the objective carboxylic acid and the distillation column, for example, may be selected from the same (similar) range with the range of the above first distillation column. Incidentally, also in the second distillation column, a hypophosphorous acid or others may be suitably fed (e.g., in the initial step of the process operation) to convert a free halogen to a hydrogen halide.

Since the lower bp fraction (or second lower bp fraction) separated from the second distillation column contains a useful component such as an alkyl halide (e.g., methyl iodide), a carboxylic acid ester (e.g., methyl acetate), and/or water, the lower bp fraction may be directly recycled to the reactor and/or second distillation column, or if necessary, may be recycled after being converted into a liquid, as same as the lower bp fraction withdrawn from the first distillation column, with a condenser or a thermal converter. Moreover, since the lower bp fraction contains an aldehyde, the lower bp fraction, for example, may be recycled after removing the aldehyde (e.g., acetaldehyde) with the aldehyde-separating column, if necessary.

On the other hand, since the higher bp fraction (or second higher bp fraction) separated from the second distillation column is rich in a carboxylic acid having "n+2" carbon atoms (e.g., propionic acid), an aldehyde, a carboxylic acid ester, an alkyl iodide, a metal salt, and others, the higher bp fraction may be directly discarded (or removed off). Incidentally, since the higher bp fraction further contains water or the objective carboxylic acid, if necessary, the higher bp fraction from which a carboxylic acid having "n+2" carbon atoms (and others) is removed and/or recovered may be recycled to the reaction system.

In the second distillation column, the purified carboxylic acid stream is withdrawn by side cut, and the position of the side stream port may be usually at a middle or lower position of the distillation column. Incidentally, by withdrawing the carboxylic acid stream from the side stream port existing at an upper position relative to the bottom port for withdrawing the higher bp fraction, the side stream and the higher bp fraction may be efficiently separated.

In order to reduce the concentration of the hydrogen halide existing in the second distillation column, at least one component (B) (second component) selected from the group consisting of (b-1) an alcohol having "n" carbon atom(s) corresponding to the objective carboxylic acid having "n+1" carbon atoms, (b-2) an ester of the alcohol with the carboxylic acid having "n+1" carbon atoms, (b-3) an alkali metal hydroxide, (b-4) an alkali metal acetate, and (b-5) a hypophosphorous acid (in particular, at least one member selected from the group consisting of the alcohol, the alkali metal hydroxide, the alkali metal acetate, and the hypophosphorous acid), and if necessary, water may be fed to the second distillation column. In particular, feeding the alkali metal hydroxide to the second distillation column realizes the remarkable decrease of the concentration of the hydrogen halide. The alkali metal hydroxide may include potassium hydroxide, sodium hydroxide, and others. The alkali metal hydroxide is usually fed as an aqueous solution in many cases. Further, in order to reduce the concentration of the hydrogen halide, the alcohol and/or the ester may be fed together with the alkali metal hydroxide. The alcohol and/or the ester may be fed together with water. Moreover, as the alkali metal acetate, there may be exemplified potassium acetate, sodium acetate, and others. From the viewpoint of convenience in handling, the alkali metal acetate or the hypophosphorous acid may be usually fed as an aqueous solution. Incidentally, acetic acid, methanol and/or methyl acetate may be used as the solvent instead of water.

The feeding position of the second component, and if necessary water, is not limited to a specific one, and may be any position in the height (or longitudinal) direction of the distillation column. The second component, and if necessary water, is usually fed from at least one position selected from the upper and lower positions relative to the side stream port in which the objective carboxylic acid stream is obtained by side cut in many cases. Feeding the alkali metal hydroxide (aqueous solution) from the lower position relative to the side stream port achieves to reduce the amount of the hydrogen halide contaminating to the carboxylic acid stream obtained by side cut in a trace amount. Feeding the alkali metal hydroxide (or aqueous solution thereof) from the upper position relative to the side stream port realizes to further reduce the contamination amount of the hydrogen halide to the carboxylic acid stream obtained by side cut.

The feeding amount of the alkali metal hydroxide may be, for example, (i) about 1 to 20,000 mol, preferably about 100 to 20,000 mol (e.g., about 200 to 15,000 mol), and more preferably about 300 to 10,000 mol (e.g., about 500 to 5,000 mol) relative to 1 mol of the hydrogen halide contained in the carboxylic acid stream (the carboxylic acid stream fed to the second distillation column). Moreover, the feeding amount of the alkali metal hydroxide may be in such a range that, for example, (ii) relative to 1 mol of the alkali metal hydroxide, the proportion of the carboxylic acid having "n+1" carbon atoms contained in the carboxylic acid stream (the carboxylic acid stream fed to the second distillation column) may be about 30 to 300,000 mol, preferably about 300 to 200,000 mol, and more preferably about 3,000 to 100,000 mol. The feeding amount of the alkali metal hydroxide may satisfy at least one of the above range of either (i) or (ii), and usually may satisfy both ranges of (i) and (ii) practically.

Moreover, the total of the feed proportion of the alcohol (b-1) and the feed proportion of the ester (b-2) may be, for example, (i) about 1 to 10,000 mol, preferably about 10 to 6,000 mol (e.g., 100 to 5,000 mol), and more preferably about 500 to 5,000 mol relative to 1 mol of the hydrogen halide contained in the carboxylic acid stream (the carboxylic acid stream fed to the second distillation column). Moreover, the above total of the feed proportions may be (ii) about 0.02 to 50% by mol, preferably about 0.1 to 30% by mol (e.g., 1 to 25% by mol), and more preferably about 1.5 to 20% by mol either relative to the total amount of the carboxylic acid having "n+1" carbon atoms contained in the carboxylic acid stream (the carboxylic acid stream fed to the second distillation column) or relative to the total amount of the alcohol fed to the reaction system. The total of the feed proportions may satisfy at least one of the above range of either (i) or (ii), and usually may satisfy both ranges of (i) and (ii). Incidentally, the proportion relative to the total amount of the alcohol is calculated on the assumption that the almost 100% of alcohol is converted to carboxylic acid.

The lower bp fraction from the second distillation column may be directly discarded (or removed off). Nevertheless, since the lower bp fraction from the second distillation column contains an alkyl halide (e.g., methyl iodide), an alkyl ester of a carboxylic acid (e.g., methyl acetate), a carboxylic acid, water, an aldehyde, and others, part or all of the fraction may be recycled to at least one member selected from the reaction system, the first distillation column, and the second distillation column (particularly, the reaction system). Further, after removing the aldehyde from the lower bp fraction, the aldehyde-removed fraction may be recycled. Moreover, the lower bp fraction may be reused as an absorbing solution for the offgas, or as a liquid mechanical sealing agent for the pump. Since the higher bp fraction (bottom solution) from the second distillation column contains a carboxylic acid having "n+2" carbon atoms, water, an objective carboxylic acid, and others, the higher bp fraction (bottom solution) may be directly discarded (or removed off), or may be recycled to the reaction system. Further, after removing the carboxylic acid having "n+2" carbon atoms from the higher bp fraction, the carboxylic acid-removed fraction may be recycled.

Incidentally, the concentration of hydrogen halide in the product may be adjusted or reduced by adjusting or regulating the feeding position of the carboxylic acid stream from the previous or preceding step in the first and/or second distillation column, the balance between the water concentration and the hydrogen halide concentration in the first distillation column, the feeding position of the alcohol and/or ester (and water) to the first distillation column, the feed proportion of the alcohol and/or ester in the first and second distillation column, the feed proportion of the alkali metal hydroxide in the second distillation column, and others.

According to the present invention, by adding the first component (A) and/or water to the first distillation column, the amount of the hydrogen iodide has been already reduced in the carboxylic acid stream. By feeding such a carboxylic acid stream as well as the second component (B), and if necessary water, to the second distillation column, the objective carboxylic acid can be efficiently removed (or separated). Further, the generation of by-products (e.g., alkali metal iodide) accompanying addition of the second component (B), and/or the contamination of the second component (B) to the carboxylic acid as a final product can be drastically reduced.

(Halide-Removing Step (Column))

By further providing (feeding) the side stream (carboxylic acid stream) containing a purified carboxylic acid recovered from the second distillation column by side cut to the halide-removing step, a halide (e.g., a halogenated hydrocarbon such as an alkyl halide (e.g., hexyl iodide, and decyl iodide)) can be removed, and a further purified carboxylic acid is producible.

In the halide-removing step, the halide-removing column is not necessary required, and the carboxylic acid stream may be contacted with a remover (removing agent or material)

having a halide-removability or -adsorbability (e.g., a zeolite, an activated carbon, and an ion exchange resin). In order to efficiently remove the halide from the carboxylic acid stream which is continuously obtained (in a continuous system), the ion exchange resin having halide-removability or -adsorbability, particularly the halide-removing column provided with the ion exchange resin therein is advantageously used.

The ion exchange resin is not limited to a specific one as far as having the halide-removability or -adsorbability, and is usually an ion exchange resin (usually a cation exchange resin) in which at least part of the active site (e.g., usually an acidic group such as a sulfone group, a carboxyl group, a phenolic hydroxy group, or a phosphone group) is substituted or exchanged with a metal. The metal may include, for example, at least one member selected from the group consisting of silver (Ag), mercury (Hg), and copper (Cu). The cation exchange resin as a base (substrate) may be any one of a strong acidic cation exchange resin and a weak (mild) acidic cation exchange resin, and the preferred one includes a strong acidic cation exchange resin, for example, a macroreticular ion exchange resin, and the like.

In the ion exchange resin, the proportion of the active site exchanged to the metal (or substituted with the metal) may be, for example, about 10 to 80% by mol, preferably about 25 to 75% by mol, and more preferably about 30 to 70% by mol.

At least contacting of the carboxylic acid stream from the second distillation column with the ion exchange resin (preferably passing of the carboxylic acid stream through the ion exchange resin) realizes removal of the halide. Following the contacting with (or passing through) the ion exchange resin, if necessary, the temperature of the carboxylic acid stream may be increased (or elevated) stepwise. The stepwise temperature elevation ensures to inhibit outflow or effusion of the metal from the ion exchange resin, as well as to remove the halide efficiently. In terms of principle of the acetolysis, a halide of a higher hydrocarbon (sometimes referred to as a higher halide, e.g., an iodide of a higher hydrocarbon) can be easily removed. Incidentally, the size of the higher halide, for example, even a halide having a side chain such as neopentyl group, is smaller than the pore size of the ion exchange resin, accordingly, the adverse effect such as the halide diffusion is small, and does not affect on the removal efficiency of the halide. Moreover, since the dissociation energy of such a halide is relatively small, the halide is efficiently removable. Accordingly, even the higher halide (e.g., an iodide) is also removable in a degree which does not affect the quality of the carboxylic acid, for example, at a temperature at which a hexyl halide (e.g., hexyl iodide) is removable.

Examples of the halide-removing column may include a packed column packing inside thereof at least the ion exchange resin which is exchanged with a metal, a column provided with a bed of an ion exchange resin (e.g., a bed comprising a particulate resin) (a guard bed) and the like. The halide-removing column may be provided with the metal-exchanged ion exchange resin, and in addition, other ion exchange resin (e.g., a cation exchange resin, an anion exchange resin, and a nonion exchange resin) inside thereof. In the case of putting the cation exchange resin at the side of the downstream relative to the ion exchange resin exchanged with the metal (e.g., putting the resin by packing, or putting the resin as a resin bed), even the metal is effused from the metal-changed ion exchange resin, the effused metal can be captured with the cation exchange resin and removed from the carboxylic acid stream.

The temperature of the halide-removing column may be, for example, about 18 to 100° C., preferably about 30 to 70° C., and more preferably about 40 to 60° C.

The rate of the carboxylic acid stream to be passed through is not limited to a specific one, and may be, for example, in a halide-removing column utilizing a guard bed, e.g., about 3 BV/h (bed volume per hour) to 15 BV/h, preferably about 5 BV/h to 12 BV/h, and more preferably about 6 BV/h to 10 BV/h.

Incidentally, in the halide-removing step, the carboxylic acid stream may be contacted with the metal-exchanged ion exchange resin. For example, the halide-removing column may comprise a column provided with the metal-exchanged ion exchange resin and a column provided with another ion exchange resin. For example, the halide-removing column may comprise an anion exchange resin column, and a metal-exchanged ion exchange resin column on the downstream side of the anion exchange resin column, or may comprise a metal-exchanged ion exchange resin column, and a cation exchange resin column on the downstream side of the metal-exchanged ion exchange resin column. The details of the former example can be referred by WO02/062740, and others.

(Aldehyde-Separating Column)

In the case where the fraction containing an aldehyde (e.g., an aldehyde having "n+1" carbon atoms) generated by the reaction is recycled and circulated to the reaction system, the distillation column(s), and others, the amount of by-product such as a carboxylic acid having "n+2" carbon atoms, an unsaturated aldehyde having "n+2" carbon atoms, and an alkyl iodide having "n+1" carbon atoms increases. Therefore, by separating the aldehyde having "n+1" carbon atoms from the lower bp fraction withdrawn from the first and/or second distillation column(s) prior to the recycle to the reaction system and/or the distillation column(s), generation of the carboxylic acid having "n+2" carbon atoms, the unsaturated aldehyde having "n+2" carbon atoms, and the alkyl iodide having "n+1" carbon atoms can be inhibited.

That is, the lower boiling point fraction withdrawn from the first distillation column and/or the second distillation column containing the alkyl halide, the alkyl ester of the carboxylic acid having "n+1" carbon atoms, the aldehyde having "n+1" carbon atoms, water, and others is fed to the aldehyde-separating column. In the aldehyde-separating column, a lower boiling point fraction (a fourth lower bp fraction) containing the aldehyde is separated from a higher boiling point fraction (a fourth higher bp fraction) containing the alkyl halide, the alkyl ester of the carboxylic acid, water, and others. The aldehyde may be separated from the overhead or upper part of the aldehyde-separating column, with the offgas component such as carbon monoxide or hydrogen. The offgas component may be previously removed off with a condenser or a cooling device, prior to the separation of the aldehyde. The lower bp fractions from the first and second distillation columns are not necessarily combined for feeding to the aldehyde-separating column. The lower bp fraction from either the first or second distillation column may be fed to the aldehyde-separating column, or the lower bp fractions from both distillation columns may be individually fed to the aldehyde-separating column via different feed lines.

In the aldehyde-separating column, since the higher bp fraction obtained by removing the aldehyde as the lower bp fraction contains the alkyl halide, water, the carboxylic acid ester, the objective carboxylic acid, and the like, the higher bp fraction can be recycled to the reaction system.

As the aldehyde-separating column, for example, there may be used a conventional distillation column, e.g., a plate column, a packed column, a flash distillation column, and others.

The temperature (overhead temperature) and pressure (overhead pressure) in the aldehyde-separating column may be selected depending on the species of aldehyde and alkyl halide as well as distillation column, and is not particularly limited as far as at least an aldehyde (e.g., acetaldehyde) is separable as a lower bp fraction from the lower bp fraction(s) (the first and/or second lower bp fraction(s)) obtained in the first and/or second distillation column(s) by utilizing difference between the aldehyde and other components (particularly an alkyl halide) in boiling point. For example, in the case of using a plate column as the aldehyde-separating column for purification of acetic acid, the overhead pressure is about 10 to 1,000 kPa, preferably about 10 to 700 kPa, and more preferably about 10 to 500 kPa as an absolute pressure. In the case where the overhead pressure is too low, the separation efficiency of acetaldehyde becomes low, it is necessary to lower the temperature for condensing gaseous components efficiently, and as a result it is not preferred in cost. On the other hand, in the case where the overhead pressure is too high, the inner temperature of the column rises due to excessively added pressure, as a result there is a possibility that acetaldehyde which is condensed within the column is polymerized within the column by exposing to high temperature thereby being contaminated in the higher bp component.

Moreover, the inner temperature of the column (overhead temperature) may be, for example, about 10 to 80° C., preferably about 20 to 70° C., and more preferably about 40 to 60° C.

In the case where the aldehyde-separating column is a plate column, the theoretical number of plates may for example be about 5 to 80, preferably about 8 to 60, and more preferably about 10 to 50.

In the aldehyde-separating column, the reflux ratio may be selected from about 1 to 1,000, preferably about 10 to 800, and preferably about 50 to 600 (e.g., about 100 to 600) depending on the above-mentioned theoretical number of plates.

Incidentally, in the case where generation of the aldehyde and hydrogen is inhibited by suitably adjusting the reaction condition in the reaction system, and further the aldehyde is removed from the recycle stream from the distillation column(s) by using the aldehyde-separating column, the amount of the aldehyde in the reaction system and/or distillation column(s) can be remarkably reduced, and the amount of the by-produced carboxylic acid having "n+2" carbon atoms can be greatly reduced. Therefore, even in a stage of the carboxylic acid stream to be fed to the second distillation column, the concentration of the carboxylic acid having "n+2" carbon atoms can be decreased to the degree within the product standards of the carboxylic acid, and it is not necessary to separate the carboxylic acid having "n+2" carbon atoms in the second distillation column.

Moreover, since the amount of the formed unsaturated aldehyde having "n+2" carbon atoms is reducible, the test value of potassium permanganate can be remarkably improved without a specific treatment such as an ozonation, and for example, can be not shorter than the standard value (120 minutes).

In the present invention, the purified carboxylic acid is producible by removing impurities from the carboxylic acid stream containing the impurities such as hydrogen halides, lower bp components and/or higher bp components with at least the first and second distillation columns. The preferred production process comprises the above reaction step, the catalyst-separation step, the first distillation step, and the second distillation step. In such a method, for example, the preferred process includes one comprising (a) continuously allowing methanol to react with carbon monoxide at a hydrogen partial pressure of 5 to 100 kPa in a vapor phase of the reaction system in the presence of (i) a catalyst system comprising a metal catalyst of the group 8 metal of the Periodic Table, an alkali metal iodide and an alkyl iodide, and (ii) water in a proportion of 0.1 to 5% by weight relative to a whole liquid-phase reaction system; (b) continuously withdrawing the reaction mixture from the reaction system; (c) feeding the reaction mixture to a catalyst-separating column; (d) separating a higher bp fraction containing the metal catalyst and the alkali metal iodide, and a lower bp fraction containing acetic acid, an alkyl iodide, methyl acetate, water and propionic acid; (e) feeding the lower boiling point fraction as a carboxylic acid stream to the first distillation column; (f) separating a lower bp fraction containing part of the alkyl iodide, the methyl acetate and water, and a higher bp fraction containing part of water and propionic acid in the first distillation column with feeding water and/or at least one component (A) (first component) selected from the group consisting of methanol and methyl acetate; (g) withdrawing a side stream containing at least the acetic acid by side cut from the first distillation column; (h) feeding the side stream to the second distillation column; (i) removing a lower bp fraction containing at least part of the alkyl iodide, the methyl acetate and water, and a higher bp fraction containing at least part of water and propionic acid in the second distillation column; and (j) withdrawing a side stream containing a purified acetic acid by side cut to recover the acetic acid. Incidentally, in the case of feeding the first component (A) alone (including the case of feeding the first component (A) as the acetic acid solution thereof), the first component (A) is fed to the first distillation column from a lower position relative to a side stream port for conducting side cut of the side stream containing acetic acid.

Further, the present invention also includes a system for producing a purified carboxylic acid having "n+1" carbon atoms, comprising the first and second distillation columns. The production system may comprise, for example, the reaction system, the catalyst-separating column, the first distillation column, and the second distillation column, and if necessary, may further comprise the halide-removing column and/or the aldehyde-separating column.

INDUSTRIAL APPLICABILITY

The present invention is useful for obtaining a carboxylic acid such as acetic acid in the industrial production process, particularly useful for obtaining a highly purified carboxylic acid in the continuous production process.

EXAMPLES

The following examples are intended to describe this invention in further detail and should by no means be interpreted as defining the scope of the invention.

Examples 1 to 10 and Comparative Examples 1 to 3

(1) Reaction

With the use of a reactor having a volume 0.3 L, a continuous reaction was conducted in accordance with a flow diagram shown in FIG. 1, and the generation rate of the product was measured (Examples 1 to 4, 7, 8 and 10). The reaction conditions and the results are shown in Table 1.

TABLE 1

| Examples | Reaction conditions | | | | | | | STY | | |
|---|---|---|---|---|---|---|---|---|---|---|
| | Pressure (MPa) | Temperature (°C.) | Rh (ppm) | LiI (wt %) | $CH_3I$ (wt %) | Water (wt %) | MA (wt %) | Hydrogen partial pressure (kPa) | AC (mol/L · H) | $CO_2$ (mol/L · H) | AD (mol/L · H) |
| 1, 2 | 3.0 | 187 | 920 | 9.7 | 14.8 | 2.0 | 5.7 | 28 | 20.6 | 0.019 | 0.0053 |
| 3, 10 | 2.7 | 186 | 650 | 9.9 | 12.1 | 1.8 | 5.5 | 31 | 11.6 | 0.013 | 0.0032 |
| 4 | 3.5 | 184 | 700 | 11.1 | 14.4 | 2.6 | 7.0 | 34 | 23.0 | 0.015 | 0.0098 |
| 7 | 3.0 | 195 | 750 | 13.4 | 9.3 | 1.7 | 5.0 | 27 | 18.3 | 0.014 | 0.0098 |
| 8 | 3.0 | 194 | 850 | 14.3 | 8.3 | 2.0 | 5.1 | 27 | 19.6 | 0.015 | 0.0101 |

In the Table, "MA", "AC" and "AD" represent methyl acetate, acetic acid and acetaldehyde, respectively. Moreover, "STY" represents the space time yield.

(2) First Distillation Step

With the use of a 40 mmφ glass Oldershaw distillation column (30 plates), the reaction mixture from the reactor was fed to the distillation column from the seventh plate from the top of the column, and methanol and/or methyl acetate, and if necessary water was added from one feed port (Feed solution I) or two feed ports (Feed solutions I and II). The distillation was conducted under an atmospheric pressure at a reflux ratio of 1.1. Incidentally, a fraction withdrawn from the overhead of the column was condensed, and separated into an upper layer and a lower layer. Each of the upper and lower layers was divided into a portion for reflux and a portion to be discharged, and the former portion from each layer was subjected to reflux so as to achieve the above reflux ratio. Incidentally, there was no substantial difference between the both layers regarding the weight ratio of the former portion and the latter portion. A liquid phase was withdrawn by side cut from a position lower than the 30th plate from the top of the distillation column. Incidentally, in Examples 5 and 6 the same operation was conducted as other Examples except that a model solution containing acetic acid, hydrogen iodide, methyl iodide, methyl acetate and water was used instead of the reaction mixture and was fed to the distillation column.

Moreover, in Comparative Examples 1 and 2, a 40 mmφ glass Oldershaw distillation column (50 plates) was used, and a model solution (containing acetic acid, hydrogen iodide, methyl iodide, methyl acetate and water) was fed to the distillation column from the seventh plate from the top of the column. In Comparative Example 1, methanol, methyl acetate and water were not fed. In Comparative Example 2, methanol (Feed solution I) was added from one feed port, and the distillation was conducted under an atmospheric pressure at a reflux ratio of 3.0 and a column bottom temperature of 120.6° C. Incidentally, a fraction withdrawn from the overhead of the column was condensed, and separated into an upper layer and a lower layer. Each of the upper and lower layers was divided into a portion for reflux and a portion to be discharged, and the former portion from each layer was subjected to reflux so as to achieve the above reflux ratio. Incidentally, there was no substantial difference between the both layers regarding the weight ratio of the former portion and the latter portion. A liquid phase was withdrawn by side cut from a position lower than the 50th plate from the top of the distillation column.

The concentration of the hydrogen iodide in the reaction mixture or model solution, and the feed conditions of methanol and/or methyl acetate are shown in Table 2. The results are shown in Table 3.

TABLE 2

| | HI in Feed solution | | Feed solution I | | | | | Feed solution II | | | | |
|---|---|---|---|---|---|---|---|---|---|---|---|---|
| | (ppm) | (mmol/H) | Feed plate | Inner temperature of column (°C.) | MeOH (mmol/H) | MA (mmol/H) | Water (mmol/H) | Feed position | Inner temperature of column (°C.) | MeOH (mmol/H) | MA (mmol/H) | Water (mmol/H) |
| Ex. 1 | 89 | 0.52 | 27 | 118.6 | 4.9 | 0 | 42.2 | BTM | 120.2 | 300 | 0 | 0 |
| Ex. 2 | 89 | 0.52 | 27 | 118.6 | 4.9 | 0 | 42.2 | BTM | 120.5 | 300 | 0 | 0 |
| Ex. 3 | 52 | 0.24 | 27 | 118.1 | 4.8 | 7.4 | 21.1 | BTM | 119.0 | 300 | 0 | 0 |
| Ex. 4 | 144 | 0.92 | 27 | 118.8 | 4.8 | 7.4 | 21.1 | BTM | 121.2 | 290 | 0 | 0 |
| Ex. 5 | 167 | 0.83 | 27 | 117.9 | 4.6 | 0 | 9.8 | BTM | 119.0 | 295 | 0 | 0 |
| Ex. 6 | 219 | 1.09 | 27 | 117.6 | 4.6 | 0 | 39.7 | BTM | 119.0 | 295 | 0 | 0 |
| Ex. 7 | 150 | 0.59 | 27 | 119.6 | 4.7 | 0 | 7.2 | — | — | — | — | — |
| Ex. 8 | 150 | 0.59 | 27 | 117.6 | 4.7 | 0 | 7.2 | — | — | — | — | — |
| Com. Ex. 1 | 70 | 0.44 | — | — | — | — | — | — | — | — | — | — |
| Com. Ex. 2 | 76 | 0.47 | 43 | — | 237.0 | 0 | 0 | — | — | — | — | — |

In the Table, "MeOH" and "MA" represent methanol and methyl acetate, respectively.

TABLE 3

|   | MeOH/HI (molar ratio) | MeOH ratio (mol %) | HI removal rate (%) | Formulation of side cut solution | | |
|---|---|---|---|---|---|---|
|   |   |   |   | HI (ppm) | HI (mmol/H) | Water (ppm) |
| Ex. 1 | 575 | 1.6 | 97.1 | 5.0 | 0.0150 | 1500 |
| Ex. 2 | 575 | 1.6 | 97.1 | 5.0 | 0.0150 | 1000 |
| Ex. 3 | 1254 | 8.2 | 98.7 | 1.8 | 0.0031 | 1500 |
| Ex. 4 | 335 | 4.4 | 96.8 | 8.4 | 0.0290 | 1200 |
| Ex. 5 | 359 | — | 98.6 | 4.0 | 0.0110 | 1100 |
| Ex. 6 | 272 | — | 99.1 | 3.3 | 0.0094 | 1900 |
| Ex. 7 | 140 | 0.44 | 94.4 | 12 | 0.033 | 330 |
| Ex. 8 | 140 | 0.44 | 92.4 | 18 | 0.045 | 1700 |
| Com Ex. 1 | 0 | 0 | 44.5 | 81 | 0.244 | 122 |
| Com Ex. 2 | 505 | — | 90.2 | 15 | 0.046 | 47 |

In the Table, "MeOH/HI" represents the proportion (molar ratio) of methanol fed to the distillation column relative to hydrogen iodide in the fed reaction mixture or model solution, and "MeOH ratio" represents the ratio (mol %) of the amount of methanol fed to the distillation column relative to the amount of methanol as a raw material fed to the reactor.

Incidentally, in Examples, since the distillation was conducted at an atmospheric pressure, the inner temperature of the column was relatively low, that is, the reaction temperature of methanol treatment was low. Incidentally, in the case of conducting the above-mentioned Examples under industrial conditions in pressure distillation, since the inner temperature of the distillation column usually rises about 20 to 30° C., it is considered that the reaction rate increases about 4 to 8 times. Therefore, it is considered that the concentration of the hydrogen iodide in the solution obtained by side cut can be reduced to about 0.2 to 2 ppm.

As apparent from Tables 2 and 3, by introducing methanol from a lower position relative to at least the side cut port of acetic acid, the concentration of the iodide in the side cut solution was remarkably reduced.

(3) Second Distillation Step

With the use of a 40 mmϕ glass Oldershaw distillation column (60 plates) as a second distillation column, the solution obtained by side cut from the first distillation column was fed to the second distillation column from the 27th plate from the top of the second distillation column, and the distillation was conducted under an atmospheric pressure at a reflux ratio of 30 with feeding a potassium hydroxide (KOH) aqueous solution from one feed port (Feed solution I) or two feed ports (Feed solutions I and II) to the second distillation column (Example 10). The vapor phase is withdrawn by side cut from the 57th plate from the top of the second distillation column. Incidentally, the side cut solution in Example 3 was once pooled in a tank, and the pooled solution was used as a side cut solution from the first distillation column.

Moreover, Example 9 and Comparative Example 3 were conducted in the same manner as Example 10 except that a model solution containing acetic acid, water and hydrogen iodide (formulation: 99.8% by weight of acetic acid, 0.2% by weight of water, and 1.4 ppm of hydrogen iodide (as iodide ion)) was fed instead of the side cut solution from the first distillation column to the second distillation column.

The concentration of the hydrogen iodide in the feed solution fed to the second distillation column, and the feed conditions of the potassium hydroxide aqueous solution are shown in Table 4. The results are shown in Table 5.

TABLE 4

|   | HI in Feed solution | | Feed solution I | | | | Feed solution II | | | |
|---|---|---|---|---|---|---|---|---|---|---|
|   | (ppm) | (mmol/H) | Feed plate | Inner temperature of column (° C.) | KOH (mmol/H) | Water (mmol/H) | Feed plate | Inner temperature of column (° C.) | KOH (mmol/H) | Water (mmol/H) |
| Ex. 9 | 1.4 | 0.011 | 33 | 119.2 | 0.99 | 7.6 | — | — | — | — |
| Ex. 10 | 1.8 | 0.011 | 33 | 120.6 | 0.57 | 5.2 | BTM | 122.0 | 0.63 | 5.8 |
| Com. Ex. 3 | 1.4 | 0.011 | — | — | — | — | — | — | — | — |

TABLE 5

|   | KOH/HI (molar ratio) | HI removal ratio (%) | HI in AC product | |
|---|---|---|---|---|
|   |   |   | (ppm) | (mmol/H) |
| Ex. 9 | 88 | 30.8 | 0.900 | 0.00730 |
| Ex. 10 | 111 | 98.2 | 0.026 | 0.00019 |
| Com. Ex. 3 | — | 18.2 | 1.100 | 0.00900 |

In the Table, "KOH/HI" represents the proportion (molar ratio) of the feeding amount of potassium hydroxide relative to the amount of the hydrogen iodide in the feed solution.

Incidentally, in the above-mentioned Examples, since the distillation was conducted at an atmospheric pressure, the inner temperature of the column was relatively low, that is, the reaction temperature of potassium hydroxide treatment was low. Incidentally, in the case of conducting the above-mentioned Examples under industrial conditions in pressure distillation, since the inner temperature of the distillation column usually rises about 20 to 30° C., it is considered that the reaction rate increases about 4 to 8 times. Therefore, it is considered that the concentration of hydrogen iodide in the side cut solution can be reduced to not higher than 3 ppb.

(4) Iodide-Removing Step

The side cut solution (Example 10) obtained by the above distillation step (3) was further passed through an Ag-exchanged ion exchange resin column at 45° C. and 8 bed volume/H, and alkyl iodide impurities were removed. Thus obtained acetic acid was analyzed by an ECD-GC, and it was found that the concentration of the alkyl iodide was not higher than the limit of identification (0.3 ppb).

The finally obtained acetic acid had extremely low concentrations of both hydrogen iodide and alkyl iodide, and was sufficient as a final product.

Moreover, in the acetic acid after removing the alkyl iodide, the concentration of the propionic acid was 93 ppm, the concentration of the crotonaldehyde was not higher than 0.2 ppm, and the potassium permanganate test was 190 minutes. Accordingly, the sufficient results as a final product were obtained.

The invention claimed is:

1. A process for producing a carboxylic acid having "n+1" carbon atoms, which comprises
    feeding a carboxylic acid stream containing at least a carboxylic acid having "n+1" carbon atoms, a hydrogen halide, a lower boiling point component and a higher boiling point component to a first distillation column,
    separating a first lower boiling point fraction containing part of the lower boiling point component and a first higher boiling point fraction containing part of the higher boiling point component in the first distillation column,
    withdrawing a first side stream containing at least the carboxylic acid having "n+1" carbon atoms by side cut from the first distillation column,
    feeding the first side stream to a second distillation column,
    separating a second lower boiling point fraction containing part of the lower boiling point component and a second higher boiling point fraction containing part of the higher boiling point component in the second distillation column, and
    withdrawing a second side stream containing the carboxylic acid having "n+1" carbon atoms by side cut from the second distillation column to recover a carboxylic acid having "n+1" carbon atoms;
    which further comprises feeding
    (i) water and at least one first component (A) selected from the group consisting of an alcohol, corresponding to the carboxylic acid, having "n" carbon atom(s), and an ester of the alcohol with the carboxylic acid to the first distillation column, or
    (ii) at least one first component (A) selected from the group consisting of an alcohol, corresponding to the carboxylic acid, having "n" carbon atom(s), and an ester of the alcohol with the carboxylic acid to the first distillation column from a lower position relative to a first side stream port for conducting side cut of the first side stream containing the carboxylic acid having "n+1" carbon atoms.

2. A process according to claim 1, wherein the hydrogen halide is separated by converting to the lower boiling point component.

3. A process according to claim 1, wherein water and the first component (A) are fed to the first distillation column from an upper position relative to the first side stream port for conducting side cut of the first side stream containing the carboxylic acid having "n+1" carbon atoms.

4. A process according to claim 1, wherein, in the first distillation column, at least water is fed from an upper position relative to the first side stream port for conducting side cut of the first side stream containing the carboxylic acid having "n+1" carbon atoms, and the first component (A) is fed from a lower position relative to the first side stream port.

5. A process according to claim 1, wherein each of the feed proportion of the first component (A) and that of water satisfies the following (i), (ii), or both of (i) and (ii):
    (i) the feed proportion is 1 to 10,000 mol relative to 1 mol of the hydrogen halide contained in the carboxylic acid stream fed to the first distillation column,
    (ii) the feed proportion is 0.02 to 50% by mol relative to the total amount of the carboxylic acid having "n+1" carbon atoms contained in the carboxylic acid stream fed to the first distillation column.

6. A process according to claim 1, which comprises further feeding to the second distillation column at least one second component (B) selected from the group consisting of (b-1) an alcohol, corresponding to the carboxylic acid having "n+1" carbon atom, having "n" carbon atom(s), (b-2) an ester of the alcohol with the carboxylic acid having "n+1" carbon atoms, (b-3) an alkali metal hydroxide, (b-4) an alkali metal acetate and (b-5) a hypophosphorous acid.

7. A process according to claim 6, wherein the second component (B) is fed to the second distillation column from at least one of upper and lower positions relative to a second side stream port for conducting side cut of the second side stream containing the carboxylic acid having "n+1" carbon atoms.

8. A process according to claim 6, wherein the total of the feed proportion of the component (b-1) and the feed proportion of the component (b-2) satisfies the following (i), (ii), or both of (i) and (ii):
    (i) the total of the feed proportion of the component (b-1) and the feed proportion of the component (b-2) is 1 to 10,000 mol relative to 1 mol of the hydrogen halide contained in the carboxylic acid stream fed to the second distillation column,
    (ii) the total of the feed proportion of the component (b-1) and the feed proportion of the component (b-2) is 0.02 to 50% by mol relative to the total amount of the carboxylic acid having "n+1" carbon atoms contained in the carboxylic acid stream fed to the second distillation column.

9. A process according to claim 6, wherein the feed proportion of the component (b-3) satisfies the following (iii), (iv), or both of (iii) and (iv):
    (iii) the feed proportion of the component (b-3) is 1 to 20,000 mol relative to 1 mol of the hydrogen halide contained in the carboxylic acid stream fed to the second distillation column,
    (iv) the amount of the carboxylic acid having "n+1" carbon atoms contained in the carboxylic acid stream fed to the second distillation column is 30 to 300,000 mol relative to 1 mol of the component (b-3).

10. A process according to claim 1, which comprises
    continuously allowing an alcohol having "n" carbon atom(s) or a derivative thereof to react with carbon monoxide at a hydrogen partial pressure of 1 to 150 kPa in a vapor phase of the reaction system in the presence of a catalyst system comprising a metal catalyst component and an alkyl halide, and water in a proportion of 0.1 to 10% by weight relative to a whole liquid-phase reaction system, continuously withdrawing the reaction mixture from the reaction system, feeding the reaction mixture to a catalyst-separating column, separating a third higher boiling point fraction containing the metal catalyst component, and a third lower boiling point fraction, and feeding the third lower boiling point fraction as a carboxylic acid stream to the first distillation column.

11. A process according to claim 1, which comprises further contacting the second side stream obtained by side cut from the second distillation column with an ion exchange resin having a halide-removability or a halide-adsorbability to purify the carboxylic acid having "n+1" carbon atoms.

12. A process according to claim 10, wherein the lower boiling point fraction withdrawn from at least one of the first distillation column and the second distillation column contains an alkyl halide, an alkyl ester of a carboxylic acid having "n+1" carbon atoms, an aldehyde having "n+1" carbon atoms, and water; which the process further comprises subjecting the lower boiling point fraction to an aldehyde separation step;

separating, in the aldehyde separation step, a fourth lower boiling point fraction containing the aldehyde, and a fourth higher boiling point fraction containing the alkyl halide, the alkyl ester of the carboxylic acid, and water; and recycling the fourth higher boiling point fraction to the reaction system.

13. A process according to claim 1, which comprises continuously allowing methanol react with carbon monoxide at a hydrogen partial pressure of 5 to 100 kPa in a vapor phase of the reaction system in the presence of a catalyst system comprising a metal catalyst of the group 8 metal of the Periodic Table, an alkali metal iodide and an alkyl iodide, and water in a proportion of 0.1 to 5% by weight relative to a whole liquid-phase reaction system, continuously withdrawing the reaction mixture from the reaction system, feeding the reaction mixture to a catalyst-separating column, separating a third higher boiling point fraction containing the metal catalyst and the alkali metal iodide, and a third lower boiling point fraction containing acetic acid, an alkyl iodide, methyl acetate, water and propionic acid, feeding the third lower boiling point fraction as a carboxylic acid stream to the first distillation column, separating a first lower boiling point fraction containing at least part of the alkyl iodide, the methyl acetate and water, and a first higher boiling point fraction containing at least part of water and propionic acid in the first distillation column, withdrawing a first side stream containing at least the acetic acid by side cut from the first distillation column, feeding the first side stream to the second distillation column, separating a second lower boiling point fraction containing part of the alkyl iodide, the methyl acetate and water, and a second higher boiling point fraction containing part of water and propionic acid in the second distillation column, withdrawing a second side stream containing the acetic acid by side cut from the second distillation column to recover acetic acid, which further comprises feeding (i) water and at least one first component (A) selected from the group consisting of methanol and methyl acetate to the first distillation column, or (ii) at least one first component (A) selected from the group consisting of methanol and methyl acetate to the first distillation column from a lower position relative to a first side stream port for conducting side cut of the first side stream containing acetic acid.

14. A process according to claim 13, which comprises further feeding to the second distillation column at least one second component (B) selected from the group consisting of (b-1) methanol, (b-2) methyl acetate, (b-3) potassium hydroxide, (b-4) potassium acetate and (b-5) hypophosphorous acid.

\* \* \* \* \*